(12) United States Patent
Rosini et al.

(10) Patent No.: US 7,307,083 B2
(45) Date of Patent: *Dec. 11, 2007

(54) TETRAHYDRO-ACRIDINE AND DITHIOLANE DERIVATIVES

(75) Inventors: Michela Rosini, Castel Maggiore (IT); Vincenza Andrisano, Bologna (IT); Manuela Bartolini, Mondolfo (IT); Carlo Melchiorre, Bologna (IT)

(73) Assignee: Alma Mater Studiorum-Universita'di Bologna, Bologna (IT)

( * ) Notice: Subject to any disclaimer, the term of this patent is extended or adjusted under 35 U.S.C. 154(b) by 0 days.

This patent is subject to a terminal disclaimer.

(21) Appl. No.: 11/759,704

(22) Filed: Jun. 7, 2007

(65) Prior Publication Data

US 2007/0219241 A1    Sep. 20, 2007

Related U.S. Application Data

(63) Continuation of application No. 10/591,515, filed as application No. PCT/IT2006/000049 on Jan. 27, 2006.

(60) Provisional application No. 60/647,498, filed on Jan. 27, 2005.

(51) Int. Cl.
*C07D 221/08* (2006.01)
*A61K 31/381* (2006.01)

(52) U.S. Cl. .......................................... 514/290; 546/79
(58) Field of Classification Search .................. 546/79; 514/290
See application file for complete search history.

(56) References Cited

U.S. PATENT DOCUMENTS

| 2,811,531 A | 10/1957 | Holly et al. ................. 260/327 |
| 2,820,799 A | 1/1958 | Wagner ....................... 260/327 |
| 2,844,585 A | 7/1958 | Cavallito .................. 260/294.7 |
| 3,019,227 A | 1/1962 | Erner .......................... 260/279 |
| 3,238,224 A | 3/1966 | Ohara et al. ................. 260/327 |
| 3,326,917 A | 6/1967 | Freimiller et al. .......... 260/279 |
| 3,406,199 A | 10/1968 | Helmut et al. .............. 260/553 |
| 3,686,180 A | 8/1972 | Sutton .................... 260/279 R |
| 3,936,457 A | 2/1976 | Schwender et al. ..... 260/279 R |

(Continued)

FOREIGN PATENT DOCUMENTS

EP    0 527 687 B1    2/1993

(Continued)

OTHER PUBLICATIONS

Akkas, "Molecular Investigation Of Antioxidants On Rat Brain Tissues," *Thesis Submitted to the Graduate School of Natural and Applied Sciences of The Middle East Technical University* (2003).

(Continued)

*Primary Examiner*—Rita Desai
(74) *Attorney, Agent, or Firm*—Marshall, Gerstein & Borun LLP

(57) ABSTRACT

Compounds identified by the general formula (I) are used for the treatment of Alzheimer's disease (I)

$$X-\overset{}{\underset{(CH_2)n}{|}}-\overset{O}{\overset{\|}{C}}-R^1\diagdown Ar$$

19 Claims, 4 Drawing Sheets

U.S. PATENT DOCUMENTS

| | | | | |
|---|---|---|---|---|
| 4,739,064 | A | 4/1988 | Shaw | 546/102 |
| 5,380,920 | A | 1/1995 | Paust et al. | 560/263 |
| 5,489,694 | A | 2/1996 | Paust et al. | 549/39 |
| 5,559,113 | A | 9/1996 | Schwartz et al. | 514/252 |
| 5,670,657 | A | 9/1997 | Kojima et al. | 549/39 |
| 5,750,560 | A | 5/1998 | Christen et al. | 514/441 |
| 5,925,668 | A | 7/1999 | Biewenga et al. | 514/440 |
| 6,090,842 | A | 7/2000 | Packer et al. | 514/440 |
| 6,111,109 | A | 8/2000 | Denny et al. | 546/102 |
| 6,204,288 | B1 | 3/2001 | Pershadsingh et al. | 514/440 |
| 6,235,772 | B1 | 5/2001 | Packer et al. | 514/440 |
| 6,387,945 | B2 | 5/2002 | Packer et al. | 514/440 |
| 6,489,336 | B1 | 12/2002 | Miyamoto et al. | 514/297 |
| 6,495,690 | B2 | 12/2002 | Kulkarni et al. | 546/102 |
| 6,605,637 | B1 | 8/2003 | Harnett et al. | 514/440 |
| 6,706,722 | B2 | 3/2004 | Emig et al. | 514/269 |
| 6,844,449 | B2 | 1/2005 | Laban et al. | 549/39 |
| 7,030,251 | B2 | 4/2006 | Laban et al. | 549/39 |
| 7,109,362 | B2 | 9/2006 | Klatt et al. | 554/87 |

FOREIGN PATENT DOCUMENTS

| | | |
|---|---|---|
| EP | 0 869 126 A1 | 7/2002 |
| EP | 1 500 650 | 1/2005 |
| EP | 1 571 146 | 9/2005 |
| JP | 08-193026 | 7/1996 |
| RU | 2 039 733 C1 | 7/1995 |
| WO | WO 93/14070 | 7/1993 |
| WO | WO 93/20040 | 10/1993 |
| WO | WO 99/29693 | 6/1999 |
| WO | WO 00/50391 | 8/2000 |
| WO | WO 00/53601 | 9/2000 |
| WO | WO 00/59899 | 10/2000 |
| WO | WO 00/76505 | 12/2000 |
| WO | WO 01/25226 | 4/2001 |
| WO | WO 02/076177 | 10/2002 |
| WO | WO 03/053366 | 7/2003 |
| WO | WO 03/087035 | 10/2003 |
| WO | WO 2005/048933 | 6/2005 |
| WO | WO 2005/048945 | 6/2005 |
| WO | WO 2005/123079 | 12/2005 |
| WO | WO 2006/029115 | 3/2006 |

OTHER PUBLICATIONS

Bartolini et al., "β-Amyloid Aggregation Induced By Human Acetylcholinesterase: Inhibition Studies," *Biochem. Pharmacol.*, 65:407-416 (2003).

Carlier et al., "Potent, Easily Synthesized Huperzine A-Tacrine Hybrid Acetycholoinesterase Inhibitors," *Bioorg. Med. Chem. Lett.*, 9:2335 (1999).

Cavallito et al., "Amino-and Ammonium-Alkylaminobenzo-quinones As Curarimimetic Agents," *J. Amer. Chem. Society*, 72:2661-2665 (1950).

Cavallito, "Quaternary Ammonium Alkylaminobenzoquinoes," *Chem. Abstr.*, 53:294-295 (1959).

Cutler et al., "Review Of The Next Generation Of Alzheimer's Disease Therapeutics: Challenges For Drug Development," *Prog. Neuro-Psychopharmacol, & Biol. Psychiat.*, 25:27-57 (2001).

Gardent, "On Some Dihydro-and Tetrahydroisoquinolines Substituted In The 1 Position With Cyclane Or Cyclene Groups," *Annales Pharmaceutiques Francaises*, 18:381-393 (1960) [(In Italian) "De Quelques Dihydro-et tetrahydro-isoquinoléines substituées en 1 par des groupes cycylaniques ou cycléniques"].

Gurkan et al., "Syntheses of Novel Indole Lipoic Acid Derivatives And Their Antioxidant Effects On Lipid Peroxidation," *Arch. Pharm. Chem. Life Sci.*, 338:67-73 (2005).

Harnett et al., "Novel Lipoic Acid Analogues That Inhibit Nitric Oxides Synthase," *Bioorganic & Med. Chem. Ltrs.*, 12:1439-1442 (2002).

Luo et al., "Ruthenium Tetraamine Chemistry Of Self-Assembled Monolayers On Gold Surfaces: Substitution And Reactivity At The Monolayer Interface," *Langmuir*, 14:3602-3606, (1998).

Melchiorre et al., "Acetylcholinesterase Noncovalent Inhibitors Based On A Polyamine Backbone For Potential Use Against Alzheimer's Disease," *J. Med. Chem.*, 41:4186-4189 (1998).

Merck Index, 1137-1138, pp. 185-186, Cavallito 53:294-295 1959.

Pang et al., "Highly Potent, And Low Cost Bis-Tetrahydroaminacrine Inhibitors Of Acetylcholinesterase," *J. Biol. Chem.*, 271:23646-23649 (1996).

Rosini et al., "Prazosin-Related Compounds, Effect Of Transforming The Piperazinylquinazoline Moiety Into An Aminomethyltetrahydroacridine System On The Affinity For $\alpha_1$-Adrenoreceptors," *J. Med. Chem.* 46:4895-4903 (2003).

Rosini et al., "Rational Approach To Discover Multipotent Anti-Alzheimer Drugs," *J. Med. Chem.*, 48:360-363 (Published on Internet Web Dec. 31, 2004).

Rosini et al. "Discovery of Multipotent Drugs For The Treatment Of Alzheimer's Disease," *Key Lecture:KL10* (Jun. 2005).

Schweizer et al., "Sulfonyliminoimidazolidines. A new class of Oral Hypoglycemic Agents," *J. Med. Chem., American Chemical Society*, 26:964-970 (1983).

Shepard, "Papaverine Analogs. IV. 1-Cycloaliphatic-6,7-Dimethoxy-Isoquinolines," *J. Organic Chem.*, 19:415-418 (1954).

Stark et al., "New potent Histamine H3-Receptor Antagonists Of The Amide Type," *Eur. J. Pharma. Sci.*, Elsevier Amsterdam, NL, 3:95-104 (1995).

Stark et al., "Search For Novel Leads for Histamine H-3-Receptor Antagonists: Amine Derivates," *Pharmazie*, 52(6):419-423 (1997).

Steinberg et al., "A Hydrophobic Binding Site In Acetylcholinesterase," *J. Med. Chem.*, 18:1056-1061 (1975).

Webb, "Affinity Of Benzoquinonium And Ambenonium Derivatives For The Acetylcholine Receptor, Tested On The Electroplax, And For Acetylcholinesterase In Solution," *Biochim. Biophys. Acta*, 102:172-184 (1965).

Wurst, Slide Presentation (May 2005).

* $P < 0.05$ VS WT; # $P < 0.05$ vs AD11

TETRAHYDRO-ACRIDINE AND DITHIOLANE DERIVATIVES

TECHNICAL FIELD

The present invention concerns organic compounds (in particular aromatic compounds), organic compounds for use as medicaments, the uses of said organic compounds for the production of pharmaceutical preparations for the treatment of pathologies characterized by deposits of β-amiloid and Alzheimer's disease. The present invention also concerns a method for the synthesis of the above-mentioned compounds.

BACKGROUND ART

Alzheimer's disease (AD) is a neurodegenerative syndrome generally linked with ageing which leads patients to a progressive deterioration of their cognitive and behavioural functions. The great majority of cases of AD has causes that are currently substantially unknown. Also for this reason, today there are still no therapeutic treatments able to halt the progression of the disease, even though some drugs have recently been put on the market, aimed especially at the control of the cognitive symptoms. These drugs—Tacrine (Cognex®), Doenpezil (Aricept®) Rivastigime (Exelon®) and Galantamine (Reminyl®)—share the same action mechanism, which consists of the inhibition of acetylcholinesterase (AChE).

Although the strengthening of cholinergic neurotransmission through the inhibition of AChE is a useful approach to the treatment of cognitive symptoms associated with AD, it has recently been proposed that the loss of neurones and the consequent appearance of cognitive symptoms are the result of a cascade of biochemical events linked with the overproduction of β-amyloid protein (Aβ) in certain cerebral areas. The Aβ peptide is obtained from the proteolysis of APP, a type I membrane glycoprotein; the peptide sequence is located partly in the extracellular domain and partly in the transmembrane in pathological conditions, the APP is processed by two proteolytic enzymes, β- and γ-secretase. Due to the action of β-secretase (BACE), a membrane aspartil protease, the release of a shorter fragment (APPβ) from the membrane is obtained, while the C-terminal portion of 99 amino acids remains anchored to the membrane. The C99 in turn may be processed by another enzyme γ-secretase, giving rise to the Aβ peptide. This protein tends to aggregate, forming extracellular deposits, which give rise to the typical lesions found in the brain of AD patients: senile plaques. The presence of these plaques produces responses of an inflammatory and oxidative type in the surrounding tissue, triggering a chain of toxic events, including an increase of the phosphorylation of tau protein, due to the activation of enzymes of inflammation and to the formation of oxygenated radical species. The progression of neurodegeneration derives from the impossibility of controlling the spread of these harmful effects. It is therefore necessary to discover pharmacological instruments that are able to act as far upstream as possible in the neurodegenerative cascade. Moreover, it is important to stress that there are other pathologies besides AD characterised by Aβ deposits. These pathologies include: Down's syndrome, hereditary cerebral haemorrhage associated with amyloidosis of the "Dutch type", amyloidosis associated with chronic inflammations, amyloidosis associated with multiple myelomas and other dyscrasias of the B lymphoid haematic cells, amyloidosis associated with type II diabetes, amyloidosis associated with diseases derived from pryons such as Creutzfeldt-Jakob's disease, the Gerstmann-Straussler syndrome, Kuru disease and scrapie in sheep (WO 02/00603).

In the field of pharmaceutical products for the treatment of AD, the patent application PCT/IT03/00227 led to the identification of a new family of 2,5-bis-diamino-[1,4]benzoquinonic derivatives which have demonstrated, among other properties, relatively high activities for the treatment of AD in mammals.

From the above it is clear that there is still a considerable need to make new medicaments available for the treatment of AD.

DISCLOSURE OF INVENTION

The aim of the present invention is to provide compounds that may be advantageously used for the treatment of AD.

According to the present invention, organic compounds are supplied, organic compounds for uses as medicaments, uses of organic compounds for the treatment of AD, and methods of synthesis of these compounds as defined in the independent claims that follow and, preferably, in any one of the claims depending directly and indirectly on the independent claims.

Unless explicitly specified otherwise, the following terms have the meaning indicated below.

In the present text the term "pharmaceutically acceptable salt" means a salt that maintains the biological properties of the original compound. Non limiting examples of methods for the preparation of these salts include the following: addition of inorganic acids (for example hydrochloric acid, hydrobromic acid, sulphuric acid, phosphoric acid and similar) or organic acids (for example acetic acid, oxalic acid, maleic acid, methanesulphonic acid, salicylic acid, succinic acid, citric acid and similar) to a free base of the initial compound; substitution of an acid proton of the initial compound with metallic cation (for example a cation of an alkaline metal or of an aluminium or similar); transfer of an acid proton of the initial compound to an organic base (for example dimethylamine, triethylamine and similar) and coordination with said organic base. Unless otherwise specified, the compounds of the present invention are to be understood as comprising their pharmaceutically acceptable salts.

In this text the term "prodrug" means an agent which is converted in vivo into a pharmacologically active substance. A pro-drug may have some advantages with respect to the corresponding pharmacologically active substance. For example, it may be easier to administer to patients and/or have greater solubility and/or a better capacity to pass through the cellular membranes. The compounds of the present invention are to be understood as comprising any of their prodrugs. The compounds of the present invention may act as prodrugs of further pharmacologically active substances.

Some compounds of this text may have one or more asymmetrical centres; these compounds may therefore be produced as (R)- or (S)-stereoisomers or as their mixtures. Unless otherwise specified, the compounds identified in this text are to be understood as including both the isomers taken individually and their mixtures, racemic or of another kind. Methods for the determination of the stereochemistry and the separation of stereoisomers are known in the prior art (see, for example, Chapter 4 of "Advanced Organic Chemistry", 4$^{th}$ edition L. March, John Wiley and Sons, New York, 1992).

The compounds identified in this text may have phenomena of tautomerism and/or geometric isomerism (that is to say cis-trans isomerism); unless otherwise specified, these compounds are to be understood as comprising tautomeric and/or geometrically isomeric forms taken either individually or in mixtures.

In particular, the groups linked to a carbon of a carbon-carbon double bond may be spatially arranged with respect to the double bond in such a way as to define molecules with cis or trans isomerism. The compounds in the present text having a carbon-carbon double bond are to be understood as comprising the cis forms, the trans forms, and their mixtures.

In the present text the term "$C_x$-$C_y$" refers to a group which is understood as having from x to y atoms of carbon.

In the present text the term "aromatic" means a substituted or not substituted group having at least one ring containing from 5 to 12 members and a substantially conjugated πelectric system. In particular, the aromatic group comprises a monocyclic ring or several fused aromatic rings (that is to say, rings that share a pair of adjacent or bonded atoms). Each aromatic ring may be arylic (that is to say, in which all the members of the ring are carbon atoms) or heteroaromatic (that is to say, in which one, two or three members of the ring are chosen from N, O, S; the remaining members of the ring are carbon atoms). When the aromatic group is a substituted aromatic group, the substituting groups are from one to seven, and, preferably, they are chosen, each one independently of the others, in the group that consists of: aliphatic $C_1$-$C_4$, halogen, hydroxy, $C_1$-$C_4$ alkyl, $C_1$-$C_4$ alkoxy, aromatic, —$NH_2$, $C_1$-$C_4$ amine, $C_2$-$C_6$ alkandiamine, carbamyl, —O, nitro, cyano, cyanoalkyl $C_1$-$C_4$, nitroalkyl $C_1$-$C_4$; where the substituent contains a further aromatic, this aromatic does not have substituents containing aromatics. More preferably, the substituent(s) is(are) chosen, independently of each other, in the group consisting of: halogen, $C_1$-$C_4$ alkyl, $C_1$-$C_4$ amine, $C_1$-$C_4$ alkoxy. Non limiting examples or aromatic groups are: benzene, naphthalene, anthracene, pyrrole, furane, thiophene, imidazole, oxazole, thiazole, pyrazole, pyridine, pyrimidine, purine and carbazol. In this text it is considered that a group comprising one or more aromatic rings as defined above, linked directly to the remaining part of the molecule or with an —O—, falls under the definition of "aromatic".

In the present text the term "amine" means a group (preferably a $C_1$-$C_5$ alkyl, even more preferably a $C_1$-$C_4$ alkyl) having an aminic moiety. Non limiting examples of amines are the following: —$CH_2$—$NH(CH_3)$, —$N(CH_3)_2$, —$CH(CH_3)N(CH_3)_2$.

In the present text the term "alkandiamine" means a group (preferably a $C_1$-$C_5$ alkyl, even more preferably a $C_1$-$C_4$ alkyl) having two aminic moieties.

In the present text the term "cyano" means a group —C≡N.

In the present text the term "nitdro" means a group —$NO_2$.

In the present text the term "cyanoalkyl" means a group (preferably a $C_1$-$C_5$ alkyl, even more preferably a $C_1$-$C_4$ alkyl) having a moiety —C≡N.

In the present text the term "nitroalkyl" means a group (preferably a $C_1$-$C_5$ alkyl, even more preferably a $C_1$-$C_4$ alkyl) having a moiety —$NO_2$.

In the present text the term "aliphatic" means a non aromatic and non substituted hydrocarbon, saturated or unsaturated, linear, branched and/or cyclic. Non limiting examples of aliphatic groups are: t-butyl, ethenyl, 1- or 2-propenyl, cycloesyl.

In the present text the term "alkyl" means a saturated aliphatic (that is to say an aliphatic group without double or triple carbon-carbon bonds). Non limiting examples of alkyls are: methyl, n-propyl, t-butyl, cycloesyl.

In the present text the term "alkoxy" means an aliphatic (preferably an aliphatic $C_1$-$C_5$, even more preferably an aliphatic $C_1$-$C_4$) linked to the remaining part of the molecule through an oxygen atom. Non limiting examples of alkoxy groups are: methoxy, ethoxy In the present text the term "carbamyl-O" means a group having the formula R'R"NCOO—, wherein R' and R" are selected, each independently of the other, from the group consisting of: hydrogen, aliphatic $C_1$-$C_4$.

BRIEF DESCRIPTION OF THE DRAWINGS

The invention will now be described with reference to the enclosed drawings, which illustrate some non limiting embodiments, in which.

BEST MODE FOR CARRYING OUT THE INVENTION

Figure 1A:
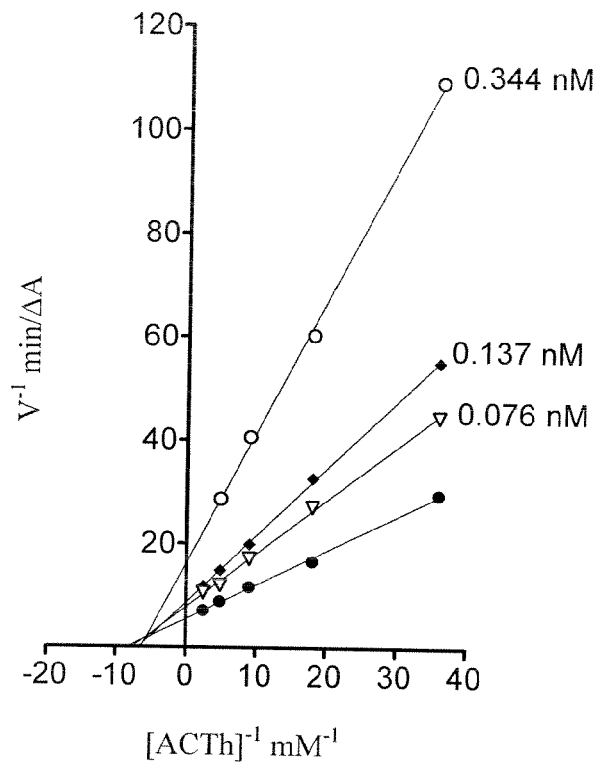
FIG. 1a describes the determination of the action mechanism for the compound 7 with the Lineweaver-Burk method (graph of the reciprocals of the initial speeds as a function of the inverse of the substrate concentration). For each concentration of the compound 7 the enzymatic activity was assessed with the variation of the concentration of the substrate acetylthiocholine (ACTh) (111-550 μM). The values of the slopes of the straight lines obtained for each inhibitor concentration were plotted on the graph (FIG. 1b) as a function of the concentration of 7 for determining the inhibiting constant $K_i$. The value of $K_i$ is given by the intercept on the axis of the abscissas and was equal to 0.155±0.046 nM.

According to a first aspect of the present invention a compound is supplied having the general formula (I):

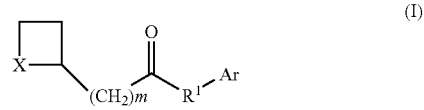

(I)

or its geometric isomers, its optically active forms, diastereoisomers, its racemic forms, or its pharmaceutically acceptable salts, wherein $R^1$ is selected from the group consisting of: alkandiamine (preferably $C_2$-$C_9$), amine (preferably $C_2$-$C_6$); X is selected from the group consisting of: —S—S—, —S—, —$CH_2$—, —$CH_2$—$CH_2$—; m is an integer greater than zero and lower than eight; Ar represents an aromatic group; $R^1$ comprises a nitrogen linked directly to the carbonyl.

According to preferred embodiments, X represents —S—S—. Preferably, m is an integer greater than two and lower than five. More preferably, m is four.

Preferably, Ar presents a formula selected from the group consisting of:

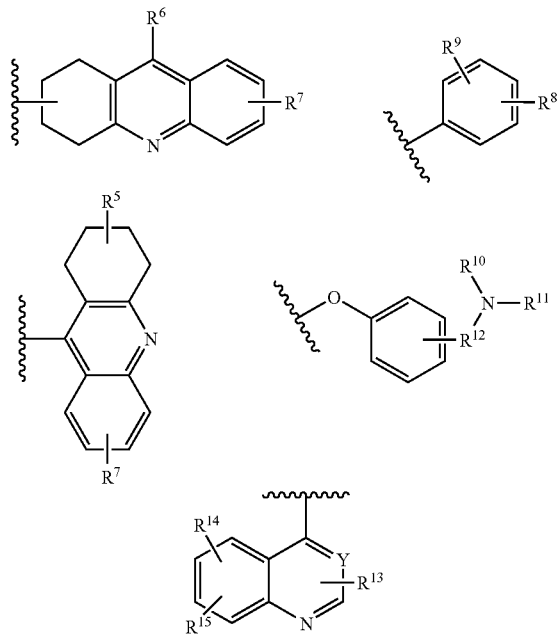

wherein $R^5$ is selected from the group consisting of: hydrogen, amine, nitroalkyl, —NH$_2$, nitro, halogen, hydroxy; $R^6$ is selected from the group consisting of: hydrogen, amine, alkandiamine, —NH$_2$; $R^7$ is selected from the group consisting of: hydrogen, group having an electron attractor inductive effect; $R^{13}$, $R^{14}$, $R^{15}$, $R^8$ and $R^9$ are chosen, each independently of the others, in the group consisting of: hydrogen, hydroxy, halogen, alkoxy, alkyl, nitroalkyl, cyanoalkyl, nitro, cyano; $R^{10}$ and $R^{11}$, are selected, each independently of the other, from the group consisting of: hydrogen, $C_1$-$C_4$ alkyl; $R^{12}$ represents a $C_1$-$C_4$ alkyl; Y is selected from the group consisting of —CH— and —N—.

More preferably, Ar presents a formula selected from the group consisting of:

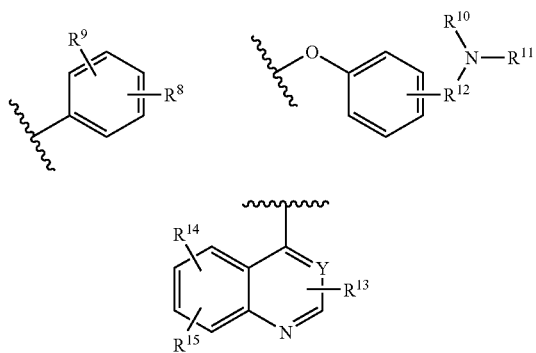

According to some particularly preferred embodiments Ar presents the formula:

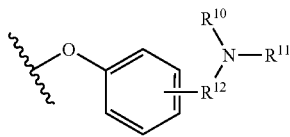

$R^1$ represents a $C_2$-$C_6$ amine.

Preferably, $R^1$ presents the formula —N(CH$_2$)$_n$—, wherein the nitrogen is directly linked to the carbonyl and n is an integer greater than one and smaller than five. More preferably, n is three; $R^{10}$ and $R^{11}$ represent, each, a respective methyl; $R^{12}$ represents an ethyl and is linked at the meta position with respect to the oxygen. Even more preferably, the compound presents the following formula:

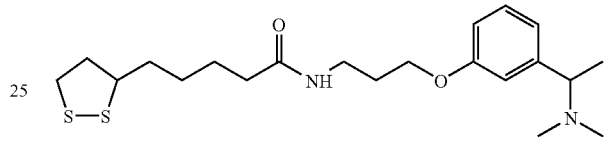

According to further particularly preferred embodiments, Ar presents the formula:

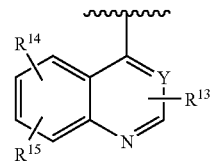

wherein Y represents N, $R^1$ represents an alkandiamine having the formula —NR$^3$—R$^2$—NR$^4$—; $R^2$ represents a $C_2$-$C_5$ alkyl; $R^3$ and $R^4$ are selected, each independently of the other, from the group consisting of: hydrogen, methyl; $R^{14}$, $R^{15}$, $R^8$ and $R^9$ are chosen, each independently of the others, in the group consisting of: hydrogen, hydroxy, halogen, $C_1$-$C_4$ alkoxy, $C_1$-$C_4$ alkyl.

Preferably, $R^2$ represents a linear propyl; $R^3$ and $R^4$ each represent a hydrogen; $R^{13}$ represents a halogen; $R^{14}$ and $R^{15}$ are selected, each independently of the other, from the group consisting of: halogen, hydroxy, $C_1$-$C_4$ alkoxy. More preferably, $R^{13}$ represents a chlorine; $R^{14}$ and $R^{15}$ represent, each, a respective methoxy.

According to further particularly preferred embodiments, Ar presents the formula:

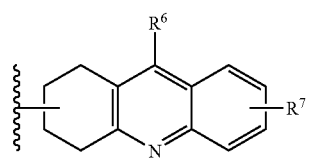

$R^7$ is selected from the group consisting of: hydrogen, $C_1$-$C_4$ alkoxy, halogen; $R^6$ is selected from the group consisting of:

—$NH_2$, alkandiamine, amine; $R^1$ represents a $C_1$ amine. Preferably, $R^6$ is selected from the group consisting of: —$NH_2$ and $C_1$-$C_4$ amine. More preferably, $R^7$ is a chlorine situated in position 6; $R^6$ represents —$NH_2$; $R^1$ represents —NH—$CH_2$—, wherein the nitrogen is linked to the carbonylic carbon.

According to further particularly preferred embodiments, Ar presents the formula:

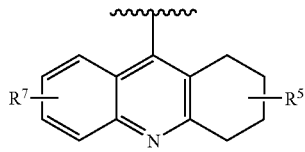

wherein $R^1$ represents a $C_2$-$C_6$ alkandiamine. Preferably, $R^1$ represents a $C_3$-$C_4$ alkandiamine. Preferably, $R^1$ presents the formula —$NR^3$—$R^2$—$NR^4$—, wherein $R^2$ represents an alkyl (preferably $C_2$-$C_4$), $R^3$ and $R^4$ are selected, each independently of the other, from the group consisting of: hydrogen, methyl. More preferably, $R^3$ and $R^4$ represent, each, a respective hydrogen; $R^2$ represents —$(CH_2)_3$—.

According to preferred embodiments, $R^7$ represents a group having an electron attractor inductive effect. Preferably, $R^7$ is selected from the group consisting of: halogen, $C_1$-$C_4$ alkoxy. More preferably, $R^7$ represents a halogen.

According to further preferred embodiments, $R^7$ is selected from the group consisting of: halogen, hydrogen, methoxy; $R^5$ is selected from the group consisting of: hydrogen, amine, nitroalkyl, halogen, hydroxy. Preferably $R^7$ is situated in position 6 according to the following formula:

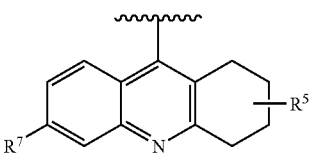

Preferably, $R^5$ is selected from the group consisting of: hydrogen, $C_1$-$C_4$ amine, $C_1$-$C_4$ nitroalkyl, —$NH_2$, nitro, halogen. More preferably, $R^5$ is selected from the group consisting of: hydrogen, halogen. Even more preferably $R^5$ represents a hydrogen.

According to preferred embodiments the compound presents the following formula:

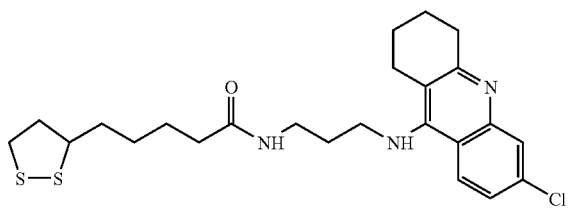

In particular, in form R:

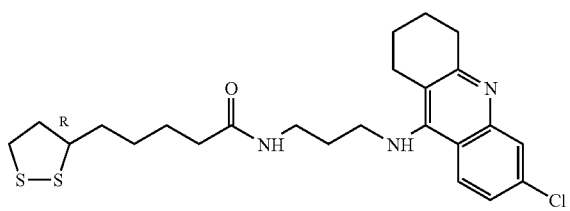

According to further particularly preferred embodiments, Ar presents the formula:

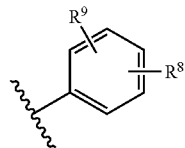

wherein $R^1$ represents a $C_3$-$C_9$ alkandiamine.

Preferably, $R^1$ represents a $C_6$-$C_8$ alkandiamine. More preferably, $R^1$ presents the formula —$NR^{16}$—$R^{17}$—$NR^{18}$—$R^{19}$—, wherein $R^{19}$ is linked to Ar and —$NR^{16}$ is linked to the carbonylic carbon; $R^{17}$ is a $C_2$-$C_7$ alkyl; $R^{16}$ and $R^{18}$ are selected, each independently of the other, from the group consisting of: $C_1$-$C_3$ alkyl, hydrogen; $R^{19}$ represents a $C_1$-$C_3$ alkyl. Even more preferably, $R^{17}$ is a $C_3$-$C_6$ alkyl; $R^{16}$ represents a hydrogen; $R^{18}$ is selected from the group consisting of: ethyl, methyl, hydrogen; $R^{19}$ represents a methyl.

Preferably, $R^9$ is selected from the group consisting of: hydrogen, hydroxy, halogen, $C_1$-$C_4$ alkoxy; $R^8$ is selected from the group: hydroxy, halogen, $C_1$-$C_4$ alkoxy. More preferably, $R^9$ represents a hydrogen and $R^8$ represents a methoxy situated in ortho or meta position (preferably ortho) with respect to the remaining part of the compound. According to preferred embodiments, $R^9$ is selected from the group consisting of: hydroxy, $C_1$-$C_4$ alkoxy; $R^8$ is selected from the group; hydroxy, $C_1$-$C_4$ alkoxy.

Particularly preferred is the compound having the formula:

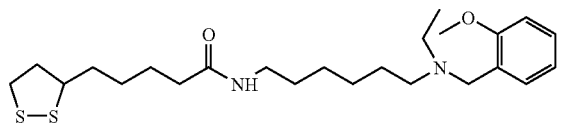

According to a further aspect of the present invention, a use of a compound having general formula (I) is supplied, as defined above for use as a medicament.

According to a further aspect of the present invention, a use of a compound having general formula (I) is supplied, as defined above for the production of a pharmaceutical preparation for the treatment of Alzheimer's disease, particularly in mammals.

According to a further aspect of the present invention, a use of a compound having general formula (I) is supplied, as defined above for the production of a pharmaceutical preparation for the treatment of pathologies characterised by deposits of β-amiloid (Aβ), particularly in mammals.

According to a further aspect of the present invention, a pharmaceutical preparation comprising a compound having general formula (I) is supplied, as defined above, or a pharmaceutically acceptable salt, thereof and an excipient and/or pharmaceutically acceptable diluent.

According to a further aspect of the present invention, a method of synthesis of a compound having general formula (I) is supplied, as defined above, comprising an addition phase wherein a compound having the general formula (II):

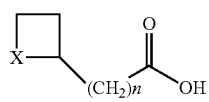

is reacted with a compound having the general formula (III):

preferably, in basic conditions.

The compounds falling within the general formula (I) may be formulated, in a known way, for parenteral administration by injection or continuous administration. Formulations for injection may be in the form of single doses, for example in ampoules or in multidose containers containing preserving agents. The composition may be in the form of a suspension, in aqueous or oily liquids, and it may contain formulation elements such as dispersing and stabilising agents. Alternatively, the active compound may be in powder form to be dissolved just before use in a suitable liquid, for example in sterilised water.

The compounds falling within the general formula (I) may be formulated for rectal administration as suppositories or enemas, for example containing excipients for suppositories of a known type, for example cocoa butter or other glycerides.

The compounds falling within the general formula (I) may also be formulated, in a known way, as compositions with prolonged release. These prolonged release compositions may be administered by implant (for example subcutaneous, or intramuscular) or by intramuscular injection. Therefore, for example, the compounds falling within the general formula (I) may be formulated with suitable polymeric or hydrophobic materials (for example an emulsion or an oil) or with ion exchange resins, or derivatives with relatively low solubility, such as salts with relatively low solubility.

For intranasal administration, the compounds falling within the general formula (I) may be formulated for administration by means of (known) device, for example in powder form with a suitable carrier.

The doses of the compounds falling within the general formula (I) will depend on the age and conditions of the patient, so the precise dose must be decided each time by the doctor. The dose will also depend on the method of administration and on the particular compound selected. Usable doses may for example be between 0.1 mg/Kg and 400 mg/Kg of body weight per day.

The compounds falling within the general formula (I) may be administered in combination with one or more suitable therapeutic agents, formulated in any known usable manner.

Further characteristics of the present invention will be seen from the following description of some examples, supplied purely as illustration without limitation.

Melting points were taken in glass capillary tubes on a Büchi SMP-20 apparatus and are uncorrected. IR, electronic impact (EI) mass, and ESI-MS spectra with direct infusion were recorded on Perkin-Elmer 297, VG 7070E, and Waters ZQ 4000 apparatus respectively. The $^1$H NMR, $^{13}$C NMR, gHSQC and COSY spectra were recorded on Mercury 400 and Varian VXR 200 and 300 instruments. Chemical shifts are reported in parts per million (ppm) relative to tetramethylsilane (TMS), and spin multiplicities are given as s (singlet), br s (broad singlet), d (doublet), dd (double doublet), t (triplet), or m (multiplet). Although the IR spectra data are not included (due to lack of unusual features), they were obtained for all the compounds listed below and were consistent with the assigned structures. The elemental composition of the compounds was within ±0.4% of the calculated value. Chromatographic separations were performed on silica gel columns by flash chromatography (Kieselgel 40, 0.040-0.063 mm; Merck) or gravity column.

EXAMPLES

The compounds 1-8 were synthesized according to the scheme below, condensing tetrahydroacridine intermediates with lipoic acid (LA).

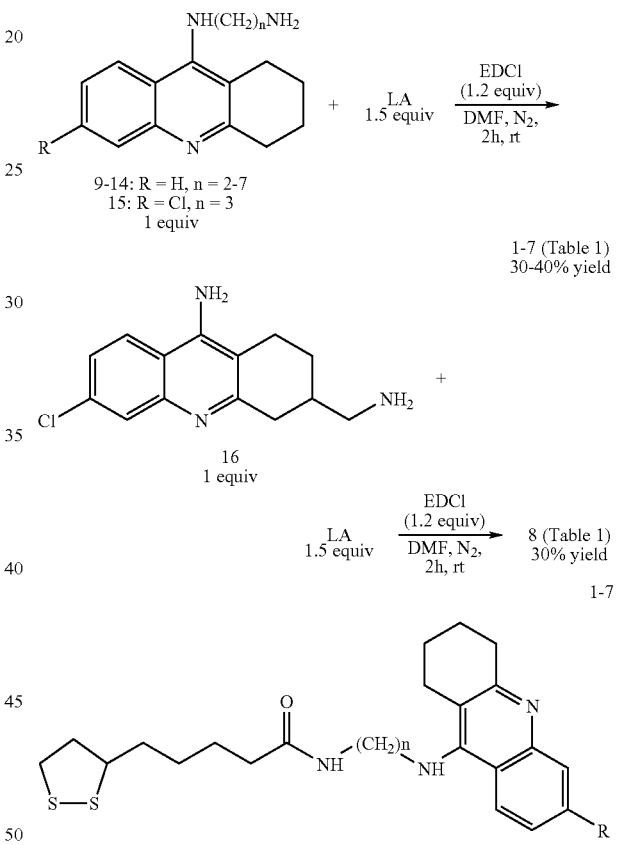

TABLE 1

| Compound | n | R |
|---|---|---|
| 1 | 2 | H |
| 2 | 3 | H |
| 3 | 4 | H |
| 4 | 5 | H |
| 5 | 6 | H |
| 6 | 7 | H |
| 7 | 3 | Cl |

Example 1

3-Aminomethyl-6-chloro-1,2,3,4-tetrahydroacridin-9-ylamine (16). The synthesis of compound 16 was achieved by condensation of 2-amino-4-chlorobenzonytril with 3-nitromethylcyclohexanone followed by reduction of the nitro group according to Rosini et al. (M. Rosini, A. Antonello, A. Cavalli, M. L. Bolognesi, A. Minarini, G. Marucci, E. Poggesi, A. Leonardi, C. Melchiorre, J. Med. Chem. 2003, 46, 4895.), and the structure was assigned by means of $^1$H NMR, $^{13}$C NMR, gHSQC, and COSY experiments. Total yield 30%; mp (melting point) 285-288° C.; $^1$H NMR (400 MHz, CD$_3$OD) δ 7.91 (d, J=8.9 Hz, 1H, C8-H), 7.58 (d, J=2.3 Hz, 1H, C5-H), 7.19 (dd, J=9.0, 2.3 Hz, 1H, C7-H), 2.86-2.94 (m, 1H, C4-H), 2.60-2.69 (m, 3H, —CH$_2$NH$_2$, C1-H), 2.19-2.25 (m, 2H, C1-H, C4-H), 2.04-2.13 (m, 1H, C2-H), 1.75-1.83 (m, 1H, C3-H), 1.29-1.39 (m, 1H, C2-H); $^{13}$C NMR (100 MHz, CD$_3$OD) δ 158.9, 150.3, 147.7, 135.2, 126.1 (C5), 124.6 (C7), 124.1 (C8), 116.3, 110.4, 48.1 (—CH$_2$NH$_2$), 38.3 (C4), 37.9 (C3), 27.3 (C2), 24.2 (C1); EI MS m/z 261 (M$^+$).

Examples 2-9

General procedure for the synthesis of compounds 1-8.

A solution of the appropriate tetrahydroacridinamine (1 eq) and lipoic acid (1.5 eq) in dry DMF (dimethylformamide) (5 mL), under N$_2$, was cooled to 0° C. and then additionated with 1-(3-dimethylaminopropyl)-3-ethylcarbodiimide hydrochloride (EDCI) (1.2 eq): the mixture was stirred at 0° C. for further 15 minutes and then at room temperature for 2 h in the dark. Solvent was then removed at reduced pressure, avoiding heating up the mixture. An oily residue was obtained which was purified by gravity column.

Example 2

5-[1,2]dithiolan-3-yl-pentanoic acid [2-(1,2,3,4-tetrahydro-acridin-9-ylamino)-ethyl]amide (1). It was synthesized from N$^1$-(1,2,3,4-tetrahydroacridin-9-yl)-ethan-1,2-diamine (9) (G. M. Steinberg, M. L. Mednick, J. Maddox, R. Rice, J Med Chem 1975, 18, 1057) (140 mg). Elution with petroleum ether/CH$_2$Cl$_2$/MeOH/aqueous 30% ammonia (6:3:1:0.055). afforded 1 as a solid foam: 35% yield; $^1$H NMR (300 MHz, CD$_3$OD) δ 8.12 (d, J=8.8 Hz, 1H), 7.78 (d, J=8.8 Hz, 1H), 7.58 (t, J=8.2 Hz, 1H), 7.39 (t, J=8.2 Hz, 1H), 3.70 (t, J=6.3 Hz, 2H), 3.28-3.39 (m, 3H), 2.93-3.15 (m, 4H), 2.71-2.79 (m, 2H), 2.26-2.40 (m, 1H), 2.15 (t, J=8.6 Hz, 2H), 1.64-1.93 (m, 5H), 1.30-1.61 (m, 6H); MS (ESI$^+$) m/z 430 (M+H)$^+$. Calculated for C$_{23}$H$_{31}$N$_3$OS$_2$: C, 64.30; H, 7.27; N, 9.78; found C, 64.41; H, 7.28; N, 9.75.

Example 3

5-[1,2]dithiolan-3-yl-pentanoic acid [3-(1,2,3,4-tetrahydro-acridin-9-ylamino)propyl]amide (2). It was synthesized from N$^1$-(1,2,3,4-tetrahydroacridin-9-yl)propane-1,3-diamine (10) (100 mg, obtained from 9-chloro-1,2,3,4-tetrahydro-acridine and propane-1,3-diamine following the procedure described in Carlier et al. (R. Carlier, D. M. Du, Y. Han, J. Liu, Y. P. Pang, Bioorg Med Chem Lett 1999, 9, 2335), and purified by flash chromatography with a gradient system of CH$_2$Cl$_2$/MeOH/aqueous 30% ammonia (9.5:0.5:0.0 to 7:3:0.1): 65% yield, $^1$H NMR (200 MHz, CD$_3$OD) δ 8.08 (d, J=8.8 Hz, 1H), 7.78 (d, J=8.7 Hz, 1H), 7.53 (t, J=8.3 Hz, 1H), 7.32 (t, J=8.3 Hz, 1H), 3.54 (t, J=6.7 Hz, 2H), 2.87-2.98 (m, 2H), 2.65 (t, J=7.5 Hz, 4H), 1.64-1.93 (m, 6H); Elution with petroleum ether/CH$_2$Cl$_2$/MeOH/aqueous 30% ammonia (5:4:1:0.05) afforded 2 as a solid foam: 35% yield; $^1$H NMR (200 MHz, CD$_3$OD) δ 8.15 (d, J=8.8 Hz, 1H), 7.78 (d, J=8.8 Hz, 1H), 7.56-7.64 (m, 1H), 7.37-7.44 (m, 1H), 3.69 (t, J=6.6 Hz, 2H), 3.40-3.52 (m, 1H), 3.23-3.36 (t, J=6.6 Hz, 2H), 2.92-3.18 (m, 4H), 2.74-2.83 (m, 2H), 2.28-2.43 (m, 1H), 2.19 (t, J=7.1 Hz, 2H), 1.73-1.95 (m, 7H), 1.22-1.68 (m, 6H); ); MS (ESI$^+$) m/z 444 (M+H)$^+$. Calculated for C$_{24}$H$_{33}$N$_3$OS$_2$: C, 64.97; H, 7.50; N, 9.47; found C, 65.18; H, 7.52; N, 9.44.

Example 4

5-[1,2]dithiolan-3-yl-pentanoic acid [4-(1,2,3,4-tetrahydro-acridin-9-ylamino)-butyl]amide (3). It was synthesized from N$^1$-(1,2,3,4-tetrahydro-acridin-9-yl)butane-1,4-diamine (11) (P. R. Carlier, D. M. Du, Y. Han, J. Liu, Y. P. Pang, Bioorg Med Chem Lett 1999, 9, 2335) (290 mg). Elution with petroleum ether/CH$_2$Cl$_2$/MeOH/aqueous 30% ammonia (6:3:1:0.06) afforded 3 as a solid foam: 38% yield; $^1$H NMR (200 MHz, CD$_3$OD) δ 8.12 (d, J=8.6 Hz, 1H), 7.78 (d, J=8.6 Hz, 1H), 7.52-7.62 (m, 1H), 7.32-7.43 (m, 1H), 3.41-3.60 (m, 3H), 2.90-3.21 (m, 6H), 2.68-2.77 (m, 2H), 2.31-2.46 (m, 1H), 2.17 (t, J=6.9 Hz, 2H), 1.38-1.95 (m, 15H); MS (ESI$^+$) m/z 458 (M+H)$^+$. Calculated for C$_{25}$H$_{35}$N$_3$OS$_2$: C, 65.60; H, 7.71; N, 9.18; found C, 65.67; H, 7.69; N, 9.15.

Example 5

5-[1,2]dithiolan-3-yl-pentanoic acid [5-(1,2,3,4-tetrahydro-acridin-9-ylamino)-pentyl]-amide (4). It was synthesized from N$^1$-(1,2,3,4-tetrahydro-acridin-9-yl)-pentane-1,5-diamine (12) (P. R. Carlier, D. M. Du, Y. Han, J. Liu, Y. P. Pang, Bioorg Med Chem Lett 1999, 9, 2335) (480 mg). Elution with petroleum ether/CH$_2$Cl$_2$/MeOH/aqueous 30% ammonia (6:3:1:0.055) afforded 4 as a solid foam: 40% yield; $^1$H NMR (200 MHz, CD$_3$OD) δ 8.09 (d, J=8.6 Hz, 1H), 7.78 (d, J=8.6 Hz, 1H), 7.52-7.60 (m, 1H), 7.33-7.41 (m, 1H), 3.40-3.57 (m, 3H), 2.87-3.18 (m, 6H), 2.63-2.75 (m, 2H), 2.25-2.43 (m, 1H), 2.17 (t, J=6.8 Hz, 2H), 1.35-1.95 (m, 17H); MS (ESI$^+$) m/z 472 (M+H)$^+$. Calculated for C$_{26}$H$_{37}$N$_3$OS$_2$: C, 66.20; H, 7.91; N, 8.91; found C, 66.41; H, 7.89; N, 8.88.

Example 6

5-[1,2]dithiolan-3-yl-pentanoic acid [6-(1,2,3,4-tetrahydro-acridin-9-ylamino)-hexyl]-amide (5). It was synthesized from N$^1$-(1,2,3,4-tetrahydro-acridin-9-yl)-hexane-1,6-diamine (13) (P. R. Carlier, D. M. Du, Y. Han, J. Liu, Y. P. Pang, Bioorg Med Chem Lett 1999, 9, 2335) (370 mg). Elution with petroleum ether/CH$_2$Cl$_2$/MeOH/aqueous 30% ammonia (6:3:1:0.05) afforded 5 as a solid foam: 30% yield; $^1$H NMR (200 MHz, CDCl$_3$) δ 7.83 (t, J=9.3 Hz, 2H), 7.47-7.56 (m, 1H), 7.28-7.37 (m, 1H), 5.89 (t, J=3.2 Hz, 1H, exchangeable with D$_2$O), 4.15 (br s, 2H, exchangeable with D$_2$O), 3.40-3.57 (m, 3H), 3.01-3.23 (m, 6H), 2.60-2.75 (m, 2H), 2.31-2.48 (m, 1H), 2.15 (t, J=7.3 Hz, 2H), 1.35-1.96 (m, 19H); MS (ESI$^+$) m/z 486 (M+H)$^+$. Calculated for C$_{27}$H$_{39}$N$_3$OS$_2$: C, 66.76; H, 8.09; N, 8.65; C, 66.87; H, 8.12; N, 8.62.

Example 7

5-[1,2]dithiolan-3-yl-pentanoic acid [7-(1,2,3,4-tetrahydro-acridin-9-ylamino)-heptyl]-amide (6). It was synthesized from N$^1$-(1,2,3,4-tetrahydro-acridin-9-yl)-heptane-1,7-diamine (14) (P. R. Carlier, D. M. Du, Y. Han, J. Liu, Y. P. Pang, Bioorg Med Chem Lett 1999, 9, 2335) (220 mg).

Elution with petroleum ether/CH$_2$Cl$_2$/MeOH/aqueous 30% ammonia (6:3:1:0.05) afforded 6 as a solid foam: 35% yield; $^1$H NMR (200 MHz, CDCl$_3$) δ 7.92 (apparent t, J=9.4 Hz, 2H), 7.51-7.61 (m, 1H), 7.30-7.41 (m, 1H), 5.57 (t, J=3.2 Hz, 1H, exchangeable with D$_2$O), 3.40-3.61 (m, 3H), 3.01-3.24 (m, 6H), 2.64-2.73 (m, 2H), 2.38-2.54 (m, 1H), 2.18 (t, J=7.3 Hz, 2H), 1.25-1.98 (m, 21H); MS (ESI$^+$) m/z 500 (M+H)$^+$. Calculated for C$_{28}$H$_{41}$N$_3$OS$_2$: C, 67.29; H, 8.27; N, 8.41; C, 67.43; H, 8.30; N, 8.39.

Example 8

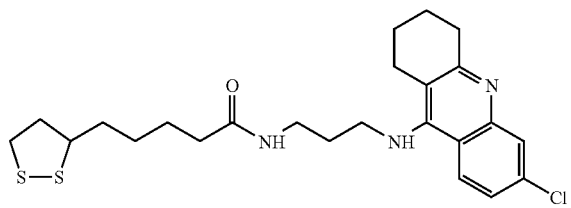

5-[1,2]dithiolan-3-yl-pentanoic acid [3-(6-chloro-1,2,3,4-tetrahydro-acridin-9-ylamino)-propyl]-amide (7). It was synthesized from N$^1$-(6-chloro-1,2,3,4-tetrahydro-acridin-9-yl)-propane-1,3-diamine (15) (180 mg) (obtained from 6,9-dichloro-1,2,3,4-tetrahydro-acridine and propane-1,3-diamine following the procedure described in Carlier et al. (see above) and purified by flash chromatography with a gradient system of CH$_2$Cl$_2$/MeOH/aqueous 30% ammonia (9.5:0.5:0.0 to 8:2:0.03): 70% yield; $^1$H NMR (200 MHz, CDCl$_3$) δ 7.93 (d, J=9.1 Hz, 1H), 7.86 (d, J=2.4 Hz, 1H), 7.22 (dd, J=9.0, 2.3 Hz, 1H), 3.62 (t, J=6.8 Hz, 2H), 2.88-3.05 (m, 4H), 2.60-2.68 (m, 2H), 1.71-1.95 (m, 6H)). Elution with petroleum ether/CH$_2$Cl$_2$/EtOH/aqueous 30% ammonia (7:2:1:0.03) afforded 7 as a solid foam: 35% yield; $^1$H NMR (200 MHz, CD$_3$OD) δ 8.08 (d, J=8.9 Hz, 1H), 7.72 (d, J=2.1 Hz, 1H), 7.28 (dd, J=8.9, 2.1 Hz, 1H), 3.42-3.58 (m, 3H), 3.27 (t, J=6.5 Hz, 2H), 2.89-3.17 (m, 4H), 2.65-2.77 (m, 2H), 2.27-2.43 (m, 1H), 2.19 (t, J=7.2 Hz, 2H), 1.73-1.91 (m, 7H), 1.31-1.65 (m, 6H); MS (ESI$^+$) m/z 478 (M+H)$^+$. Calculated for C$_{24}$H$_{32}$ClN$_3$OS$_2$: C, 60.29; H, 6.75; N, 8.79; found C, 60.45; H, 6.74; N, 8.77.

Example 9

5-[1,2]dithiolan-3-yl-pentanoic acid (9-Amino-6-chloro-1,2,3,4-tetrahydro-acridin-3-ylmethyl)-amide (8).

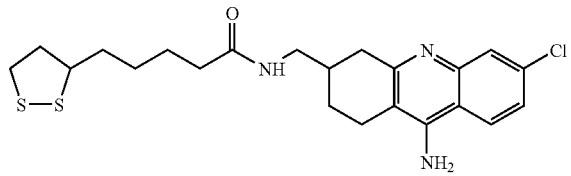

It was synthesized from 16 (150 mg). Elution with CH$_2$Cl$_2$/toluene/EtOH/aqueous 30% ammonia (5:3:2:0.02) afforded 8 as a solid foam: 30% yield; $^1$H NMR (200 MHz, CD$_3$OD) δ 8.09 (d, J=8.9 Hz, 1H), 7.72 (d, J=2.2 Hz, 1H), 7.36 (dd, J=9.2, 2.2 Hz, 1H), 3.50-3.62 (m, 2H), 2.96-3.21 (m, 4H), 2.70-2.83 (m, 1H), 2.38-2.69 (m, 3H), 2.28 (t, 7.0 Hz, 2H), 2.05-2.21 (m, 2H), 1.79-1.95 (m, 1H), 1.23-1.78 (m, 7H); EI MS m/z 449 (M$^+$). Calculated for C$_{22}$H$_{28}$ClN$_3$OS$_2$: C, 58.71; H, 6.27; N, 9.34; found C, 58.91; H, 6.26; N, 9.31.

Example 10

N-(9-Amino-6-chloro-1,2,3,4-tetrahydro-acridin-3-yl-methyl)-2-[1,2]dithiolan-3-yl-acetamide (17).

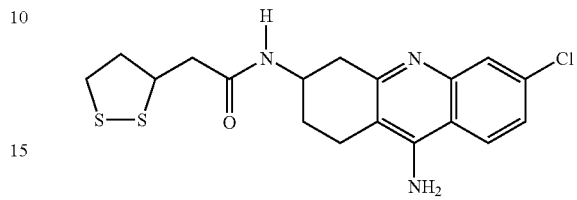

A solution of 16 (140 mg, 0.53 mmol) and [1,2]dithiolan-3-yl-acetic acid (Chen, Yaun-Shek and Lawton, Richard G. An efficient synthetic route to 2-(1,2-dithiolan-3-yl)acetic acid. Trisnorlipoic acid and amide derivatives. Tetrahedron Letters 1997, 38, 5785-5788) (90 mg, 0.55 mmol) in anhydrous DMF (5 mL), under N$_2$, was cooled to 0° C. and then additioned with 1-(3-dimethylaminopropyl)-3-ethylcarbodiimide hydrochloride (EDCI) (113 mg, 0.59 mmol); the reaction mixture was stirred at 0° C. for 15 min and then at room temperature for 2 h in the dark. Solvent was then evaporated, accurately avoiding heating up the mixture. An oily residue was obtained which was purified by gravity column. Elution with petroleum ether/CH$_2$Cl$_2$/MeOH/aqueous 30% ammonia solution (5:4:1:0.1) afforded 17 as a waxy solid: 40% yield; $^1$H NMR (200 MHz, CD$_3$OD) δ 8.03 (d, J=9.2 Hz, 1H), 7.67 (d, J=2.2 Hz, 1H), 7.30 (dd, J=8.8, 2.2 Hz, 1H), 4.05 (m, 1H), 2.95-3.34 (m, 5H), 2.46-2.59 (m, 6H), 1.99-2.20 (m, 3H), 1.48-1.52 (m, 1H). Anal. Calculated for C$_{19}$H$_{22}$ClN$_3$OS$_2$: C, 55.93; H, 5.44; N, 10.30. Found: C, 56.01; H, 5.45; N, 10.11.

Example 11

5-[1,2]dithiolan-3-yl-pentanoic acid {6-[Ethyl-(2-methoxy-benzyl)-amino]-hexyl}-amide (18)

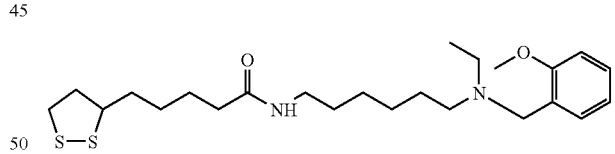

It was synthesized from N$^1$-ethyl-N1-(2-methoxy-benzyl)-hexane-1,6-diamine (patent application PCT/IT03/0227) (300 mg, 1.13 mmol) and lipoic acid (350 mg, 1.70 mmol) following the procedure described for 17, and purified by gravity column. Elution with a gradient of mobile phase petroleum ether/toluene/CH$_2$Cl$_2$/EtOH/aqueous 30% ammonia solution (7:2:1:1:0.05 to 7:1:1:1:0.5) afforded 18 as a waxy solid: 43% yield, $^1$H NMR (200 MHz, CDCl$_3$) δ 7.42-7.48 (m, 1H); 7.18-7.26 (m, 1H), 6.85-6.99 (m, 2H), 5.43 (br t, 1H, exchangeable with D$_2$O), 3.84 (s, 3H), 3.53-3.64 (m, 1H+s, 2H), 3.08-3.27 (m, 4H), 2.43-2.57 (m, 5H), 2.17 (t, J=7.4 Hz, 2H), 1.82-2.00 (m, 1H), 1.29-1.73 (m, 14H), 1.07 (t, J=7.0 Hz, 3H); MS (ESI$^+$) m/z 453 (M+H)$^+$. Anal. Calculated for C$_{24}$H$_{40}$N$_2$O$_2$S$_2$: C, 63.67; H, 8.91; N, 6.19. Found: C, 63.79; H, 8.93, N, 6.17.

Examples 12-14

Compound 19 was synthesized according to the scheme below

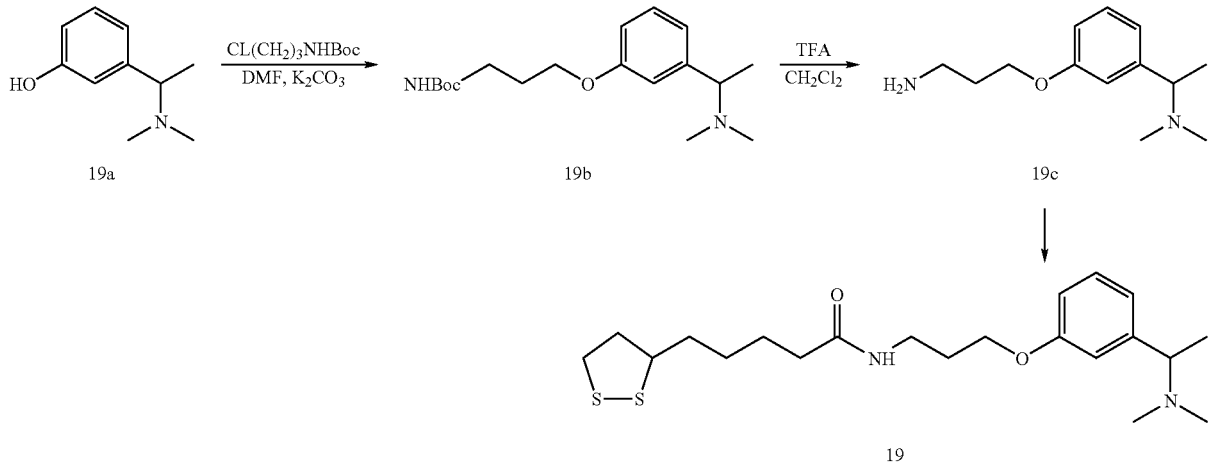

Example 12

{2-[3-(1-dimethylamino-ethyl)-phenoxy]-ethyl}-carbamic acid ter-butyl ester (19b). A solution of 19a was synthesized following the procedure described for the corresponding (R,S)-3-[[1-di-($^2$H$_3$)methylamino]ethyl]phenol in: Ciszewska, Grazyna; Pfefferkorn, Heidi; Tang, Y. S.; Jones, Lawrence; Tarapata, Richard; Sunay, Ustun B. Synthesis of tritium, deuterium, and carbon-14 labeled (s)-n-ethyl-n-methyl-3-[1-(dimethylamino)ethyl]carbamic acid, phenyl ester, (1)-2,3-dihydroxybutanedioic acid salt (SDZ ENA 713 hta), an investigational drug for the treatment of Alzheimer's disease. Journal of Labelled Compounds & Radiopharmaceuticals 1997, 39, 651-668) (350 mg, 2.17 mmol), (3-chloro-propyl)-carbamic acid terbutyl ester (420 mg, 2.17 mmol) and K$_2$CO$_3$ (300 mg, 2.17 mmol) in DMF (10 mL) was stirred under reflux conditions for 24 h. Evaporation of the solvent afforded a residue which was purified by gravity column. Elution with CHCl$_3$/MeOH/ aqueous 30% ammonia solution (9:1:0.02) afforded 19b as an oil: 65% yield, $^1$H NMR (200 MHz, CDCl$_3$) δ 7.20 (t, J=8.0 Hz, 1H); 6.79-6.89 (m, 3H), 4.92 (br s, 1H, exchangeable with D$_2$O), 4.02 (t, J=6.4 Hz, 2H); 3.20-3.33 (m, 3H), 2.20 (s, 6H), 1.93-1.99 (m, 2H), 1.44 (s, 9H), 1.35 (d, J=6.6 Hz, 3H).

Example 13

3-[3-(1-Dimethylamino-ethyl)-phenoxy]-propylamine (19c). A solution of 19b (200 mg, 0.62 mmol) in CH$_2$Cl$_2$ (5 mL) was additioned with TFA (trifluoroacetic acid) (1.5 mL) and stirred at room temperature for 2 h. The reaction mixture was evaporated in a vacuum, the residue obtained was dissolved in water, made basic by adding NaOH 2 N and then extracted with CHCl$_3$ (3×20 mL). Evaporation of the anhydrified solvent afforded 19c as an oil; quantitative yield, $^1$H NMR (200 MHz, CDCl$_3$) δ 7.20 (t, J=8.0 Hz, 1H); 6.72-6.88 (m, 3H), 4.04 (t, J=6.2 Hz, 2H); 3.12-3.22 (m, 1H), 2.91 (t, J=6.6 Hz, 2H), 2.19 (s, 6H), 1.88-1.95 (m, 2H), 1.43 (br s, 2H, exchangeable with D$_2$O), 1.34 (d, J=6.6 Hz, 3H).

Example 14

5-[1,2]dithiolan-3-yl-pentanoic acid {3-[3-(1-dimethylamino-ethyl)-phenoxy]-propyl}-amide (19) was synthesized from 19c (150 mg, 0.67 mmol) and lipoic acid (210 mg, 1.02 mmol) following the procedure described for 17, and purified by gravity column. Elution with petroleum ether/toluene/CH$_2$Cl$_2$/MeOH/aqueous 30% ammonia solution (6:1:1.5:1.5:0.01) afforded 19 as a waxy solid; 30% yield, $^1$H NMR (200 MHz, CDCl$_3$) δ 7.27 (t, J=8.2 Hz, 1H); 6.78-6.98 (m, 3H), 5.99 (br t, 1H); 4.09 (t, J=6.0 Hz, 2H); 3.21-3.62 (m, 5H), 3.05-3.19 (m, 3H), 2.40-2.53 (m, 1H), 2.32 (s, 6H), 2.22 (t, J=7.2 Hz, 2H); 1.81-2.0 (m, 3H), 1.65-1.73 (m, 4H), 1.47 (d, J=6.6 Hz, 3H); MS (ESI$^+$) m/z 411 (M+H)$^+$. Anal. Calculated for C$_{21}$H$_{34}$N$_2$O$_2$S$_2$: C, 61.42; H, 8.35; N, 6.82. Found: C, 61.62; H, 8.36, N, 6.80.

Examples 15-17

Compound 20 was synthesized according to the scheme below

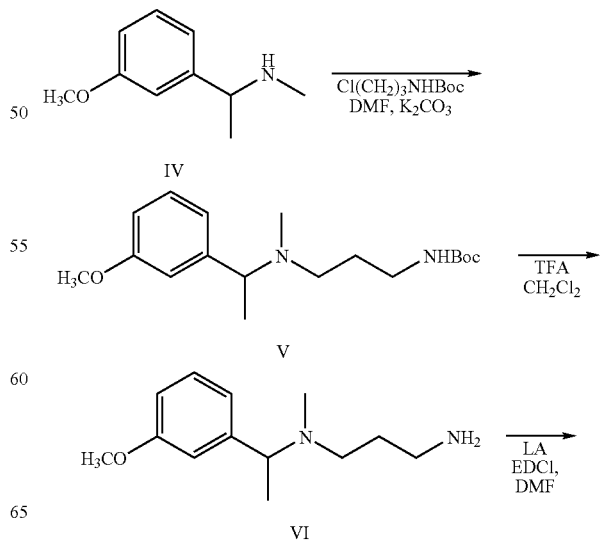

-continued

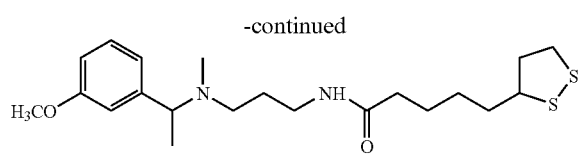

Example 15

(3-{[1-(3-methoxy-phenyl)-ethyl]-methyl-amino}-propyl)-carbamic acid ter-butyl ester (V). A solution of [1-(3-methoxy-phenyl)-ethyl]-methyl-amine (IV) (Grethe, Guenter; Lee, Hsi Lin; Uskokovic, Milan; Brossi, Arnold. Syntheses in the isoquinoline series. Synthesis of 2,3-dihydro-4(1H)-isoquinolones. Journal of Organic Chemistr 1968, 33, 491-494) (320 mg, 1.9 mmol), (3-chloro-propyl)-carbamic acid tert-butylic ester (370 mg, 1.9 mmol), $K_2CO_3$ (260 mg, 1.9 mmol) and a catalytic quantity of KI in DMF (5 mL) was stirred under reflux conditions for 24 h. Evaporation of the solvent afforded a residue which was purified by gravity column. Elution with $CHCl_3$/MeOH/aqueous 30% ammonia solution (9:1:0.005) afforded V as an oil: 40% yield, $^1$H NMR (200 MHz, $CDCl_3$) δ 7.20 (t, J=8.0 Hz, 1H); 6.74-6.95 (m, 3H), 5.38 (br s, 1H, exchangeable with $D_2O$), 3.80 (s, 3H); 3.50 (q, J=7.0 Hz, 1H), 3.13 (q, J=6.2 Hz, 2H), 2.30-2.52 (m, 2H), 2.19 (s, 3H), 1.54-1.68 (m, 2H), 1.44 (s, 9H), 1.35 (d, J=6.6 Hz, 3).

Example 16

$N^1$-[1-(3-Methoxy-phenyl)-ethyl]-$N^1$-methyl-propane-1,3-diamine (VI). It was obtained as an oil from V (230 mg, 0.62 mmol) and TFA (1.5 mL) in $CH_2Cl_2$ (5 mL) following the procedure described for 19c; quantitative yield, $^1$H NMR (200 MHz, $CDCl_3$) δ 7.27 (t, J=8.0 Hz, 1H); 6.80-6.97 (m, 3H), 3.85 (s, 3H); 3.54 (q, J=6.6 Hz, 1H), 2.74 (t, J=6.6 Hz, 2H), 2.30-2.58 (m, 2H), 2.25 (s, 3H), 1.55-1.67 (m, 2H+2H exchangeable with $D_2O$), 1.39 (d, J=7 Hz, 3H).

Example 17

5-[1,2]dithiolan-3-yl-pentanoic acid (3-{[1-(3-methoxy-phenyl)-ethyl]-methyl-amino}-propyl)-amide (20) was synthesized from V (130 mg, 0.59 mmol) and lipoic acid (240 mg, 1.47 mmol) following the procedure described for 17, and purified by gravity column. Elution with petroleum ether/$CH_2Cl_2$/EtOH/aqueous 30% ammonia solution (5.5:3.5:1:0.015) afforded 20 as a waxy solid; 55% yield, $^1$H NMR (200 MHz, $CDCl_3$) δ 7.23 (t, J=7.8 Hz, 1H); 6.75-6.90 (m, 3H), 6.56 (br s, 1H, exchangeable with $D_2O$); 3.79 (s, 3H); 3.47-3.58 (m, 2H), 3.05-3.25 (m, 4H), 2.37-2.45 (m, 3H), 2.20 (s, 3H), 2.03 (t, J=7.2 Hz, 2H); 1.82-1.97 (m, 1H), 1.38-1.73 (m, 8H), 1.34 (d, J=6.4 Hz, 3H); MS (ESI$^+$) m/z 411 (M+H)$^+$. Anal. Calculated for $C_{21}H_{34}N_2O_2S_2$: C, 61.42; H, 8.35; N, 6.82. Found: C, 61.65; H, 8.36, N, 6.81.

Example 18

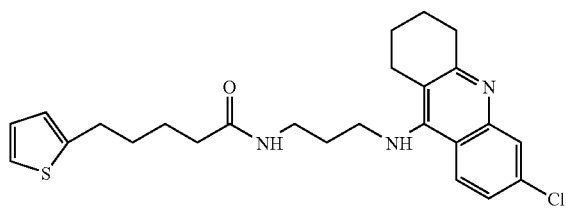

5-thiofen-2-yl-pentanoic acid [3-(6-chloro-1,2,3,4-tetrahydro-acridin-9-ylamino)-propyl]-amide (21) was synthesized from 15 (350 mg, 1.21 mmol) and 5-thiofen-2-yl-pentanoic acid (334 mg, 1.82 mmol) following the procedure described for 17, and purified by flash chromatography. Elution with petroleum ether/$CH_2Cl_2$/MeOH/aqueous 30% ammonia solution (6:3.5:0.5:0.007) afforded 21 as a waxy solid; 80% yield, $^1$H NMR (200 MHz, $CDCl_3$) δ 7.96 (d, J=8.8 Hz, 1H), 7.88 (d, J=2.2 Hz, 1H), 7.23 (d, J=1.8 Hz, 1H), 7.09-7.11 (m, 1H), 6.91 (t, J=3.6 Hz, 1H), 6.76-6.78 (m, 1H), 6.05 (br t, 1H, exchangeable with $D_2O$); 3.48-3.52 (m, 4H), 3.02-3.05 (m, 2H), 2.85 (t, J=6.6 Hz, 2H), 2.71-2.76 (m, 2H), 2.25 (t, J=6.6 Hz, 2H), 1.71-1.90 (m, 10H); MS (ESI$^+$) m/z 456 (M+H)$^+$. Anal. Calculated for $C_{25}H_{30}ClN_3OS$: C, 65.84; H, 6.63; N, 9.21. Found: C, 65.61; H, 6.65, N, 9.18.

Examples 19-20

Compound 23 was synthesized according to the scheme below

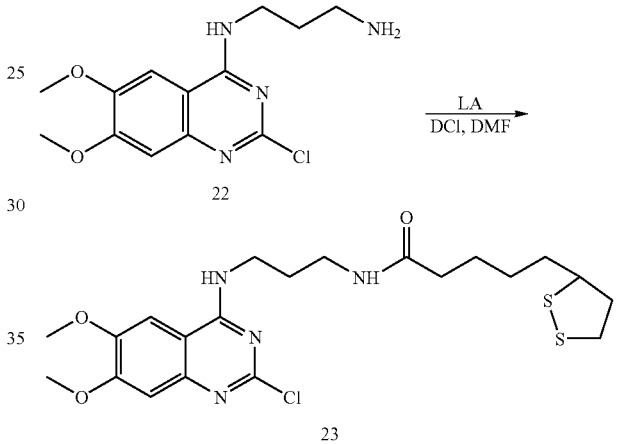

Example 19

$N^1$-(2-Chloro-6,7-dimethoxy-chinazoline-4-yl)-propan-1,3-diamine (22). A solution of 2,4-dichloro-6,7-dimethoxychinazoline (1.0 g, 3.86 mmol) in 20 mL of anhydrous THF (tetrahydrofuran) was additioned with propanediamine (0.57 g, 7.72 mmol) and stirred at room temperature under $N_2$ for 16 h. After evaporation of the solvent the residue obtained was purified by flash chromatography with mobile phase gradient $CH_2Cl_2$/MeOH/aqueous 30% ammonia solution (9:1:0 to 9:2:0.2) affording 22 as a solid: 75% yield; mp: 215° C. dec; $^1$H NMR (300 MHz, $CDCl_3$) δ 8.61 (br s, 1H, exchangeable with $D_2O$), 7.13 (s, 1H), 6.99 (s, 1H), 3.99 (s, 3H), 3.96 (s, 3H), 3.77-3.81 (m, 2H), 3.10-3.13 (m, 2H), 1.86-1.89 (m, 2H), 1.69 (br s, 2H, exchangeable with $D_2O$).

Example 20

5-[1,2]dithiolan-3-yl-pentanoic acid [3-(2-chloro-6,7-dimethoxy-chinazoline-4-ylamino)-propyl]-amide (23) was synthesized from 22 (400 mg, 1.35 mmol) and lipoic acid (556 mg, 2.70 mmol) following the procedure described for 17, and purified by gravity column. Elution with mobile phase petroleum ether/toluene/$CH_2Cl_2$/MeOH/aqueous 30% ammonia solution (5:4.5:0.5:0.008) afforded 15 as a waxy solid: 30% yield; $^1$H NMR (300 MHz, $CDCl_3$) δ 7.51 (br s, 1H exchangeable with D$_2$O), 7.36 (s, 1H), 7.14 (s, 1H), 6.32 (br s, 1H, exchangeable with D$_2$O), 4.06 (s, 3H), 4.01 (s, 3H), 3.72-3.75 (m, 2H). 3.47-3.63 (m, 1H), 3.43-3.46 (m, 2H), 3.13-3.23 (m, 2H), 2.41-2.52 (m, 1H), 2.33 (t, 2H), 1.44-1.96 (m, 9H); MS (ESI$^+$) m/z 485 (M+H)$^+$, 507 (M+Na)$^+$. Anal. Calculated for C$_{21}$H$_{29}$ClN$_4$O$_3$S$_2$: C, 52.00; H, 6.03; N, 11.55. Found: C, 52.231; H, 6.15, N, 11.67

Example 21

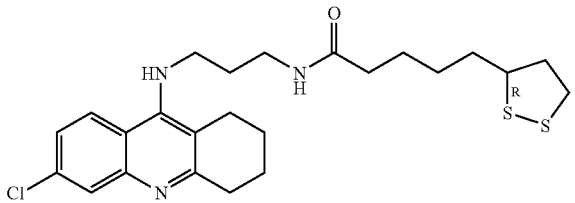

5-(R)-[1,2]dithiolan-3-yl-pentanoic acid [3-(6-chloro-1,2,3,4-tetrahydro-acridin-9-yl)amino]-propyl}-amide (24) was synthesized as described for the corresponding racemic compound (7) from R-(+)-1,2-dithiolan-3-pentanoic acid and presents the same spectroscopic and chemical-physical characteristics.

Example 22

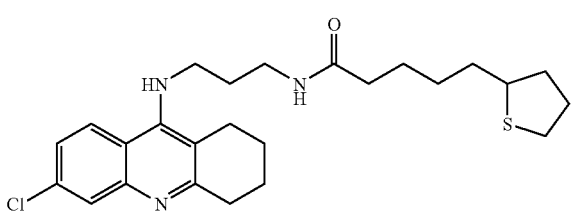

5-(tetrahydrithiofen)-2-yl-pentanoic acid [3-(6-chloro-1,2,3,4-tetrahydro-acridin-9-yl)amino]-propyl}-amide (25) was synthesized as described for the preceding compounds from 6-(2-tetrahydrothienyl)-valeric acid (Kursanov, D. N. Ionic Hydrogenation and Related Reactions. Harwood Academic Pub. 1985) and from N$^1$-(6-chloro-1,2,3,4-tetrahydro-acridin-9-yl)-propane-1,3-diamine following the procedure described for 17, and purified by flash chromatography. Elution with petroleum ether/CH$_2$Cl$_2$/MeOH/aqueous 30% ammonia solution (5:4.5:0.5:0.05) afforded the product as a waxy solid; 10% yield, $^1$H NMR (200 MHz, CDCl$_3$) δ 7.98 (d, 1H), 7.72 (d, 1H), 7.28 (d, 1H), 6.05 (br t, 1H, exchangeable with D$_2$O), 5.07 (br t, 1H, exchangeable with D$_2$O), 3.48-3.52 (m, 3H), 3.27-3.31 (m, 2H), 2.85-3.16 (m, 4H), 2.71-2.76 (m, 2H), 2.27-2.41 (m, 3H), 1.51-1.90 (m, 15H); MS (ESI$^+$) m/z 460 (M+H)$^+$. Anal. Calculated for C$_{25}$H$_{34}$ClN$_3$OS: C, 65.26; H, 7.45; N, 9.13. Found: C, 65.71; H, 7.55, N, 9.41.

Example 23

Determination of inhibiting power on HuAChE and BChE

The activity of the compounds examined, expressed as IC$_{50}$, was assessed according to the Ellman spectrophotometric method (Ellman G. L., Courtney K. D., Andrei V., Featherstone R. M. Biochem. Pharmacol. 1961, 7, 88-95] on human recombinant acetylcholinesterase (E.C. 3.1.1.7) (AChE or HuAChE) and butyrylcholinesterase (E.C. 3.1.1.8) (BChE) from human serum. The IC$_{50}$ values represent the inhibitor concentrations necessary to reduce the enzymatic activity by 50% and are the mean of two independent measurements, each in duplicate.

TABLE 2

Inhibiting activity on human recombinant AChE and on BChE from human serum

| Compound | IC$_{50}$ AChE (M) | IC$_{50}$ BChE (M) |
|---|---|---|
| 1 | (9.70 ± 0.36) 10$^{-8}$ | (4.75 ± 0.18) 10$^{-8}$ |
| 2 | (6.96 ± 0.45) 10$^{-9}$ | (1.20 ± 0.06) 10$^{-8}$ |
| 3 | (3.52 ± 0.22) 10$^{-8}$ | (5.04 ± 0.32) 10$^{-9}$ |
| 4 | (3.84 ± 0.23) 10$^{-8}$ | (1.48 ± 0.35) 10$^{-9}$ |
| 5 | (3.01 ± 0.15) 10$^{-8}$ | (3.24 ± 0.29) 10$^{-9}$ |
| 6 | (3.27 ± 0.13) 10$^{-8}$ | (8.58 ± 0.57) 10$^{-9}$ |
| 7 | (2.53 ± 0.16) 10$^{-10}$ | (1.08 ± 0.25) 10$^{-8}$ |
| 24 | (2.30 ± 0.15) 10$^{-10}$ | |
| 8 | (2.32 ± 0.23) 10$^{-7}$ | |
| 17 | (2.15 ± 0.08) 10$^{-7}$ | (2.58 ± 0.06) 10$^{-6}$ |
| 15 | (2.15 ± 0.08) 10$^{-8}$ | (2.58 ± 0.06) 10$^{-6}$ |
| Tacrine | (4.24 ± 0.21) 10$^{-7}$ | (4.58 ± 0.30) 10$^{-8}$ |
| LA | >10$^{-3}$ | >10$^{-3}$ |
| 21 | (2.66 ± 0.23) 10$^{-9}$ | (3.06 ± 0.07) 10$^{-8}$ |
| 18 | (2.56 ± 0.08) 10$^{-7}$ | (2.49 ± 0.11) 10$^{-6}$ |
| 19 | (2.52 ± 0.17) 10$^{-5}$ | (8.24 ± 0.65) 10$^{-5}$ |
| 20 | (7.41 ± 0.37) 10$^{-5}$ | (3.98 ± 0.24) 10$^{-7}$ |
| 23 | (1.92 ± 0.25) 10$^{-4}$ | |

Example 24

Inhibition of β-amyloid aggregation (1-40) induced by human recombinant AChE

The inhibiting activity on the aggregation of the β-amiloid peptide (1-40) induced by human recombinant AChE was detected with a fluorimetric method based on the use of Thioflavin T (Bartolini, M.; Bertucci, C.; Cavrini, V.; Andrisano, V. β-Amyloid aggregation induced by human acetylcholinesterase: inhibition studies. Biochem. Pharmacol. 2003, 65, 407-416). The compounds were tested at a fixed concentration of 100 µM and the values of the % inhibition of AChE-induced Aβ40 aggregation are given in Table 3.

TABLE 3

Inhibition of AChE-induced Aβ40 aggregation

| Compound [ ] 100 µM | % of inhibition ± SEM |
|---|---|
| Tacrine | <5 |
| LA | <5 |
| LA + Tacrine | 15 ± 6 |
| 15 | 25 ± 5 |
| LA + 15 | 30 ± 7 |
| 24 | 68 ± 3 |
| 21 | 24.1 ± 5.7 |
| 23 | 32.1 ± 3.9 |
| 18 | 16.8 ± 2.2 |
| 19 | 9.0 ± 6.6 |
| 20 | 15.6 ± 7.8 |
| 7 | 61.8 ± 0.8 |

In 7 the IC$_{50}$ value was also determined, which was 45.0±14.6 µM (Rosini M. et al. J Med Chem 2005, 48, 360-363)

7 proved to be only 3 times less powerful than propidium, one of the most powerful inhibitors of AChE-induced Aβ40 aggregation (Bartolini, M.; Bertucci, C.; Cavrini, V.; Andrisano, V. b-Amyloid aggregation induced by human acetylcholinesterase: inhibition studies. Biochem. Pharmacol. 2003, 65, 407-416); propidium presents an $IC_{50}$ value of 12.6±0.5 μM. Moreover, 7 and its enantiomer 24 proved to be significantly more powerful than other classic AChE inhibitors approved for the treatment of AD (Bartolini, M.; Bertucci, C.; Cavrini, V.; Andrisano, V. beta-Amyloid aggregation induced by human acetylcholinesterase: inhibition studies. Biochem. Pharmacol. 2003, 65, 407-416).

Example 25

Determination of the action mechanism and of the inhibition constant ($K_i$). The assessment of the kinetics of an inhibitor supplies important information concerning the nature of enzyme-inhibitor interaction, the binding sites and the quantitative efficacy of the bond, expressed by the $K_i$. The $K_i$ describes the state of equilibrium between a free enzyme (in the particular case human recombinant AChE), an inhibitor (in the particular case the compound 7) and the enzyme-inhibitor complex, representing the constant of dissociation of the enzyme-inhibitor complex. To obtain an estimate of the competitive inhibition constant $K_i$, the Lineweaver-Burk method was used. For each concentration of the compound 7 (interval 0-0.344 nM) the enzymatic activity was assessed with the variation of the acetylthiocholine substrate concentration (111-550 μM). The data obtained were plotted on a graph according to the Lineweaver-Burk method, that is indicating the reciprocal of the enzymatic velocity (1/v) as a function of the reciprocal of the substrate concentration (1/[ACTh)]. The Lineweaver-Burk graphs concerning TC (tacrine) inhibition (not shown) and 7 both show straight lines with increasing slopes in which may be noted a variation both of the value of $V_{max}$ and of $K_m$ in the presence of increasing concentrations of inhibitor. This behaviour indicates a mixed type of competitive inhibition, which implies a significant interaction of the inhibitor both with the free enzyme and with the acetylated enzyme.

The inhibiting behaviour of 7, as deduced from FIG. 1a, is very similar to that shown by some known bis-tetrahydroaminoacridine inhibitors of AChE. These compounds bind simultaneously with the catalytic and peripheral sites of AChE and are characterised by an enzyme inhibiting mechanism of a mixed type. (Pang, Y. P.; Quiram, P.; Jelacic, T.; Hong, F.; Brimijoin, S. Highly potent, selective, and low cost bis-tetrahydroaminacrine inhibitors of acetylcholinesterase. Steps toward novel drugs for treating Alzheimer's disease. J. Biol. Chem. 1996, 271, 23646-23649). From these results it may be deduced that the compound 7 is able to bind both with the active site of AChE and with an accessory site, potentially represented by the peripheral anionic site of the enzyme.

Figure 1B:
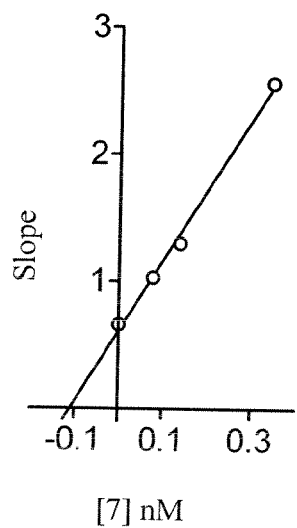

The values of the slopes of the lines shown in FIG. 1a were then plotted on a graph as a function of the concentration of 7 (FIG. 1b) or of TC. The intercept on the axis of the abscissas of the line obtained gives the value of $K_i$ for the compound examined, that is for 7 or TC, which is respectively $K_i$=0.155±0.046 nM or $K_i$=0.151±0.016 μM.

Example 26

The toxic effects of the compounds LA, 7 and 15 were first determined with the colorimetric MTT assay in SH-SY5Y cells similar to human neuronal cells, as described by Mosmann et al. (Mosmann, T. Rapid colorimetric assay for cellular growth and survival: application to proliferation and cytotoxicity assays. J. Immunol. Methods 1983, 65, 55-63).

The measurements were taken with a spectrophotometer (TECAN®, Spectra model Classic, Salzburg, Austria) at a wavelength of 405 nm. The cellular viability was expressed as a percentage of control cells and calculated by the formula $F_t/F_{nt} \times 100$, where $F_t$=absorbance of treated neurones and $F_{nt}$=absorbance of non treated neurones.

The SH-SY5Y cells were routinely grown at 37° C. in a humidified incubator with 5% $CO_2$ in Dulbecco's modified Eagle's medium supplemented with 10% foetal calf serum (FCS), glutamine 2 mM, penicillin U/mL and streptomycin 50 μg/mL.

Figure 2:
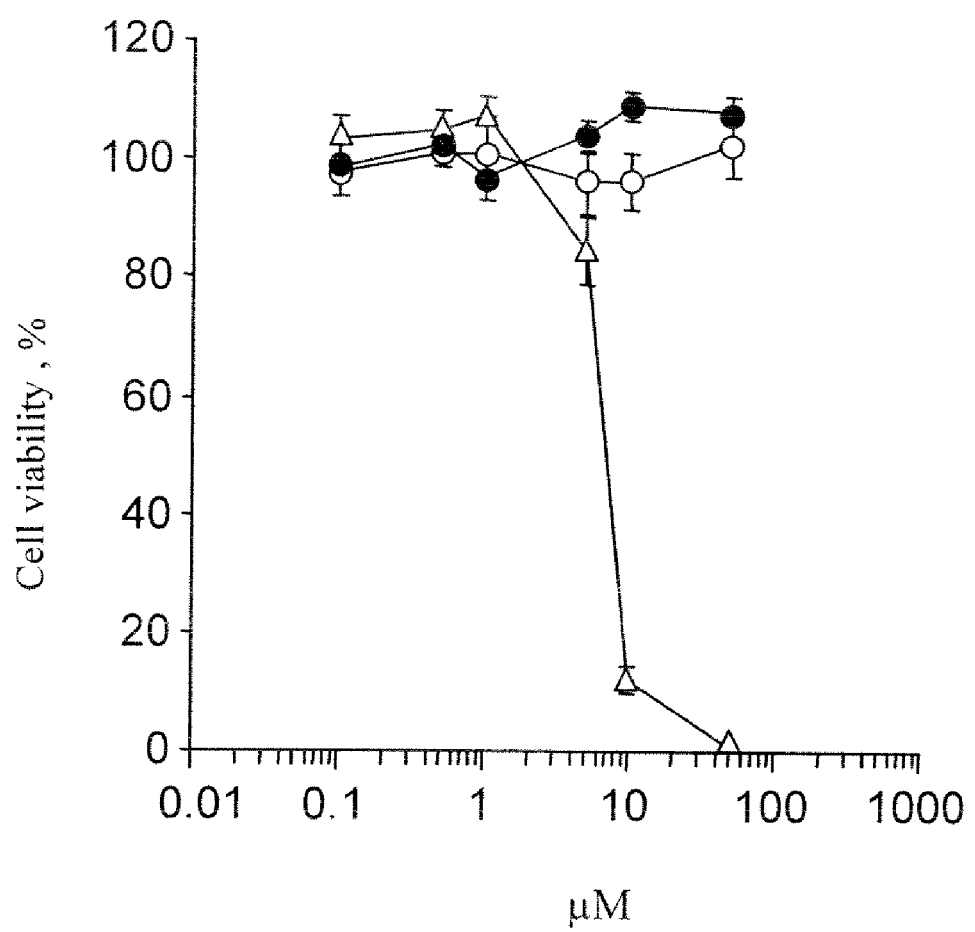
FIG. 2 shows the effects of the compounds on cellular vitality in the neuronal cells; the cellular vitality was determined by testing with 3-(4,5-dimethyl-2-thiazolyl)-2,5-diphenyl-2H-tetrazole bromide (MTT) (as described in example 26), after 24 hours of incubation with different concentrations of lipoic acid (LA) (full circle), 7 (open circle) and 15 (open triangle). The results are expressed as a percentage of cells with respect to the control. The values have been given as a mean ±SD (standard deviation) of three independent experiments.

As shown in FIG. 2, the treatment of SH-SY5Y cells with LA and 7 (0.1-50 μM) did not lead to variations in cellular viability. On the contrary, the treatment of SH-SY5Y cells with 15 (0.1-50 μM) produced a strong decrease of cellular viability for concentrations of 10 μM (88%) and 50 μM (99%).

Example 27

The intracellular antioxidant activity of LA, 7 and 15 was evaluated by measuring the formation of intracellular reactive oxygen species (ROS) evoked by exposure of SH-SY5Y cells (the cell cultures were treated as described in example 26) to ter-butyl hydroperoxide (t-BuOOH), a compound used to induce oxidative stress. The formation of intracellular ROS was determined using a fluorescent probe, DCFH-DA, as described by Wang H. et al. (H. Wang, J. A. Joseph, Free Radic. Biol. Med. 1999, 27, 612).

An interval of concentrations of the tested compounds was used which would not modify their cellular viability (0.1-50 μM for LA and 7; 0.1-5 μM for 15). As shown in Table 4, the treatment of SH-SY5Y cells with LA showed a significant decrease in (p<0.01) of ROS formation only with the highest concentration used (50 μM), while the treatment with 7 produced an inhibiting effect in ROS formation which depended strongly on the concentration of 7. Significant inhibiting effects were obtained with concentrations of 7 or 5 μM (p<0.01), 10 μM and 50 μM (for both p<0.001). When treated with 15 (0.1-5 μM), the cells did not show any difference as regards ROS formation. Taken all together, these results showed that the compounds LA and 7 do not influence cellular vitality, whereas 15 has a neurotoxic effect. Moreover, LA and 7 (but not 15) are able to protect the neuronal cells against ROS formation (64% inhibition).

TABLE 4

| | % intracellular ROS | | |
|---|---|---|---|
| μM | LA | 15 | 7 |
| 0 | 86.00 ± 9.46 | 86.00 ± 9.46 | 86.00 ± 9.46 |
| 0.1 | 91.25 ± 2.99 | 88.75 ± 8.41 | 99.50 ± 3.54 |
| 0.5 | 90.25 ± 6.65 | 95.00 ± 5.20 | 99.67 ± 7.02 |
| 1 | 83.00 ± 7.58 | 77.00 ± 8.76 | 96.67 ± 8.02 |
| 5 | 79.50 ± 8.06 | 61.67 ± 9.02* | 82.50 ± 7.78 |
| 10 | 74.33 ± 3.51 | 51.25 ± 9.21** | tox[b] |
| 50 | 58.50 ± 9.19* | 30.50 ± 9.04** | tox[b] |

The results are expressed as the percentage increase of intracellular ROS determined by the treatment with tert-butyl hydroperoxide. Data are reported as the mean±SD (standard deviation) of three tests independent of one another (treated against not treated; *p<0.01, **p<0.001). [b]tox=cytotoxicity.

Example 28

Assay for the analysis of BACE activity
Materials
BACE1 (β-secretase) purified and expressed in Baculovirus in 50 mM Tris HCl (pH=7.5), 10% glycerol (5 Units)
Substrate: Rhodamine-EVNLDAEFK-quencher (750 nM in 50 mM ammonium bicarbonate)
Reference inhibitor: peptide derivative of statin (H-Lys-Thr-Glu-Glu-Ile-Ser-Glu-Val-Asn-[Statina(3S,4S)]-Val-Ala-Glu-Phe-OH) (concentration interval: 70-6 nM)
Assay buffer: 50 mM Sodium Acetate, pH=4.5
BACE1 solution stop: 2.5 M Sodium Acetate
Instrumentation
Fluoroskan Ascent multi-well spectrofluorimeter ($\lambda_{excitation}$: 544 nm; $\lambda_{emisssion}$: 590 nm)
Cliniplate black multi-well plate (96 wells)
Analysis protocol
1. 20 μL of substrate were added to 20 μL of the compound to be tested (or to the buffer if preparing the control well)
2. To start the reaction, 20 μL of BACE1 enzyme were added to the well.
3. The mixture was incubated at 37° C. for 60 minutes.
4. 20 μL of the solution were added to stop the reaction. Then the fluorescence signal was read.
Results
BACE activity was measured with a fluorimetric analysis method using a multi-well spectrofluorimeter. The peptide substrate of the analysis mimes the APP protein which is the natural substrate of BACE. The synthetic substrate contains two groups: a group that donates fluorescence (a derivative of rhodamine, D) and a group that quenches fluorescence, A. The weakly fluorescent substrate becomes highly fluorescent after the enzyme cut; the increase in fluorescence is linearly related to the speed of proteolysis.

In optimised analysis conditions (incubation time: 60 minutes, temperature: 37° C., $\lambda_{excit}$=544 nm, $\lambda_{emiss}$=590 nm, Substrate: 250 nM, Enzyme 1 U/mL) the assay allowed the measurement of the activity of BACE-1 and its inhibition by assessing the fall in the fluorescence signal.

The intensity of the fluorescence signals with and without the inhibitor were compared and the percentages of inhibition due to the presence of growing concentrations of the compound to be tested were calculated with the following expression: $100-(IF_i/IR_o \times 100)$ where $IF_i$ and $IF_o$ are the intensities of the fluorescence signal obtained for BACE-1 respectively in the presence and absence of the inhibitor. The inhibition curves were obtained for each compound by plotting on a graph the inhibition percentages obtained with respect to the logarithm of the inhibitor concentration. The linear regression parameters were determined and, when possible, the value of $IC_{50}$ was extrapolated (GraphPad Prism 3.0 GraphPad Software Inc.).

To demonstrate the validity of the assay, a reference inhibitor (a peptide derivative of statin) was diluted in various concentrations in the reaction wells ($IC_{50}$=18 nM). The value of $IC_{50}$ was calculated using GraphPad Prism software.

The BACE-1 activity was inhibited by 7 in a concentration-dependent mode at nanomolar concentration levels. Table 5 shows the $IC_{50}$ value of 7 and of the drugs currently used for the treatment of AD. Among these, only Donepezil showed a BACE inhibiting strength comparable to that of 7.

TABLE 5

| Compound | $IC_{50}$ (nM) on BACE | Range of concentration (nM) |
|---|---|---|
| 7 | 69.7 | 760-8 |
| Donepezil | 170.1 ± 32.7 | 500-3 |
| Tacrine | not active at 4000* | 4000-40 |
| Galantamine | not active at 5000* | 5000-1000 |
| Rivastigmine | not active at 3000* | 3000-300 |

Example 28

In order to check the efficacy of 7, 19, 20 and 18 in improving the degeneration due to AD, these compounds were administered to anti-NGF mice.

This animal model (anti-NGF) (Ruberti F, et al., J Neurosci 2000, Vol. 20, pp. 2589-2601) presents a phenotype highly similar to AD in man. In particular, the model consists of a transgenic mouse which expresses antibodies for the nervous growth factor (NGF), and consequently shows an extensive loss of neurones in the cortex, formation of β-amyloid plaques and of intracellular neurofibrillary tangles, as well as behavioural dysfunctions. In particular, in order to produce anti-NGF transgenic mice (AD11), the variable regions in the light and heavy chains of the anti-NGF monoclonal antibody αD11 were linked to the constant human regions k and γ1, to give the man/rat chimeric antibody αD11, and they were then placed under the transcriptional control of the promoter of the precocious region of the human cytomegalovirus (CMV). Mice expressing functional anti-NGF antibodies (AD11 mice) were obtained by crossing mice that expressed the light chain (CMV-VK αD11) with mice that expressed the heavy chain (CMV-VH αD11).

The dose (expressed in mM of solution) was chosen in order to demonstrate that the efficacy of these compounds is better than that of the compounds from which they are derived. For this reason Memoquin (the compound indicated with XVI in the patent application PCT/IT03/00227), which is known for improving all the phenotypic markers in anti-NGF mice (AD11), was administered in a dose which, based on previous studies, was expected to give only a partial recovery on the phenotype.

Moreover, to assess the direct contribution of lipoic acid (LA) alone, in comparison with that of the conjugate of lipoic acid, and to exclude that the effects observed might be due to lipoic acid, this too was administered to the anti-NGF mice. The treatment pattern shown below was therefore followed.

TABLE 6

| Compound | n. | Admin | Dosage | Duration |
|---|---|---|---|---|
| 15 | 3 | i.p. | 0.1 mg/kg/day (0.104 mM) | 15 |
| 7 | 4 | i.p. | 0.165 mg/kg/day (0.104 mM) | 15 |
| Memoquin | 3 | i.p. | 3.5 mg/kg/day (1.658 mM) | 15 |
| 18 | 4 | i.p. | 2.5 mg/kg/day (1.658 mM) | 15 |
| Riva. | 4 | i.p. | 0.5 mg/kg/day (0.37 mM) | 15 |
| 19 | 5 | i.p. | 0.52 mg/kg/day (0.37 mM) | 15 |
| 20 | 4 | i.p. | 0.52 mg/kg/day (0.37 mM) | 15 |
| LA | 4 | i.p. | 0.254 mg/kg/day (0.37 mM) | 15 |
| LA | 4 | i.p. | 1.14 mg/kg/day (1.658 mM) | 15 |

In table 6: Riva. indicates rivastigime; n. indicates the number of mice; i.p. indicates that the compound was administered by intraperitoneal injection; the duration of the treatment is expressed in days; the molarity refers to the molarity of the solution administered to the anti-NGF mice.

After the treatment, the mice were anaesthetised with 2,2,2-tribromoethanol (8 μL/g of body weight) and the encephala were removed from the cranial box. The front part of the brain, containing the basal forebrain and one of the two occipital poles was fixed in 4% paraformaldehyde, cryoprotected in 30% saccarose and treated for immunohistochemistry. The second occipital pole was frozen on dry ice and treated so as to be subjected to Western blot to assess the presence of phosphorylated tau.

Immunohistochemistry was carried out to show the number of cholinergic neurones in the basal forebrain. For this purpose, sections were incubated with the monoclonal antibody anticholine acetyltransferase (1:500, Chemicon International Inc., Temecula, Calif.). The reaction was developed using the avidin-biotin alkaline phosphatase Elite Standard kit (Vector laboratories, Burlingame, Calif.), followed by a development with 3,3' diaminobenzidine HCl (Sigma, Sant Louis, Mo.) and 5-bromo-4-chloro-3-indolyl phosphate toluidine salt (Sigma).

To carry out a Western Blot analysis an iced solution was prepared (50 mm Tris-HCl, pH 7.5, 50 mM EDTA, 250 mM Spermidine, 1 mM phenylmethylsulphonyl fluoride (PMSF), 1 mM iodoacetamide, 10 μg/mL leupeptin, 1 μg/mL aprotinine, 4 μg/mL soybean trypsin inhibitor, 10 μg/mL turkey egg white inhibitor, 0.1% Triton X-100).

The homogenates were centrifuged at 13,400×rpm for 30 minutes at 4° C., collecting the surnatant, re-centrifuged and kept at −80° C. until use. The proteic content was determined by diluting the samples ten times and using the BIO-RAD "DC protein assay kit" (Hercules, Calif., USA). The samples (20 μg protein) were loaded on polyacrylamide gel NuPAGE 10% (Invitrogen, Carlsbad, Calif.) and a SDS-PAGE and a Western blot were carried out in order to detect phosphorylated tau. In particular, phosphorylated tau. was found using monoclonal antibodies AT270 (1:1000, Innogenetics, Gand, Belgium) which detect the phosphorylated tau in the Thr181 residue. A prestained proteic marker (New England Biolabs, Ipswich, Mass.) was loaded to find the dimension of the bands. The reaction was developed using an anti-mouse HRP (1:5000, GE Healthcare, Little Chalfont, England) and a developing solution ECL (GE Healthcare).

Results

Figure 3:
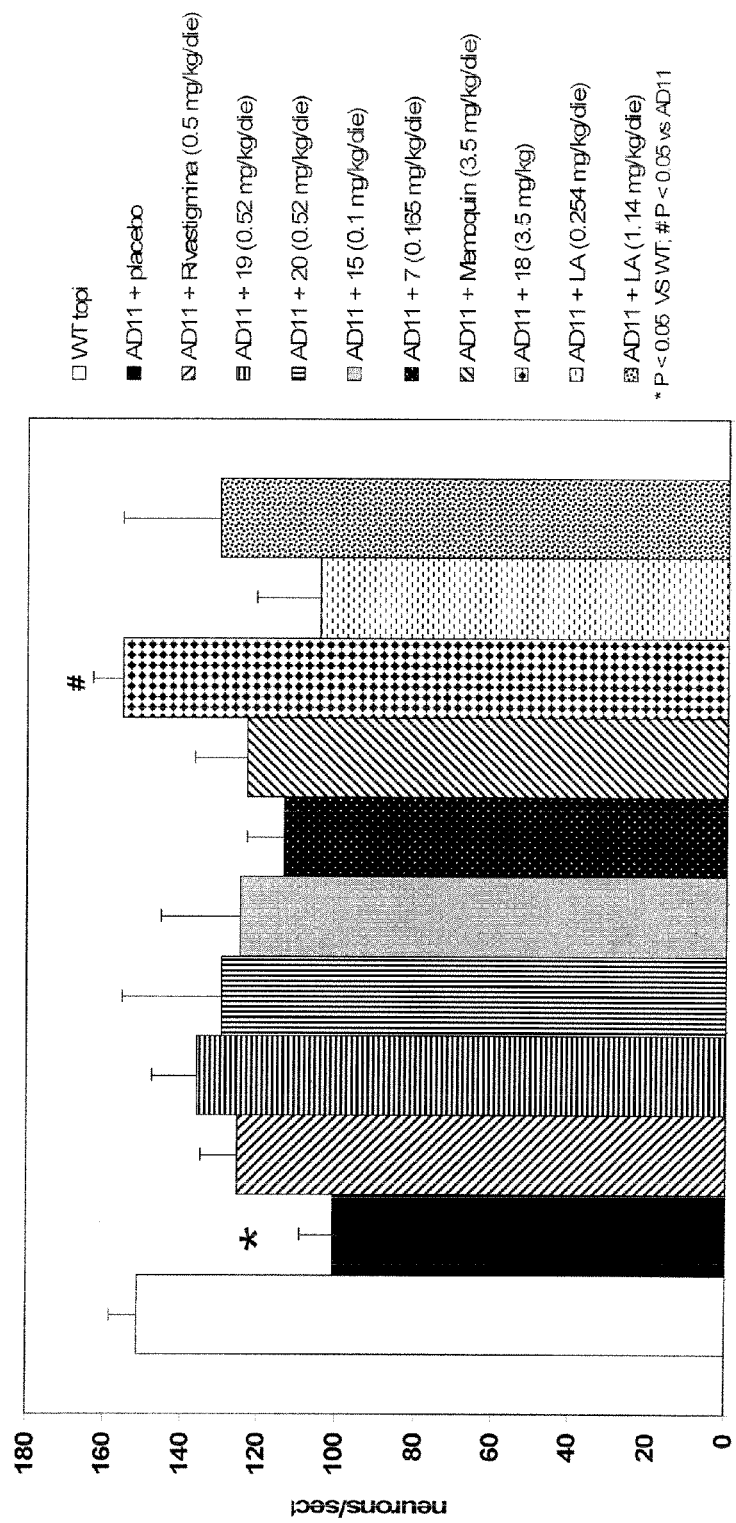
FIG. 3 shows the effects of the compounds on the cholinergic deficit of anti-NGF mice, * and # P<0.05.

The administration of LA, tacrine, 7, 19, 20, rivastigmine and Memoquin did not allow the complete recovery of the cholinergic deficit of the anti-NGF mice. The only compound that allowed a significant recovery, from a statistical point of view, of the number of cholinergic neurones in the basal forebrain was 18 (P<0.05; FIG. 3).

Figure 4:
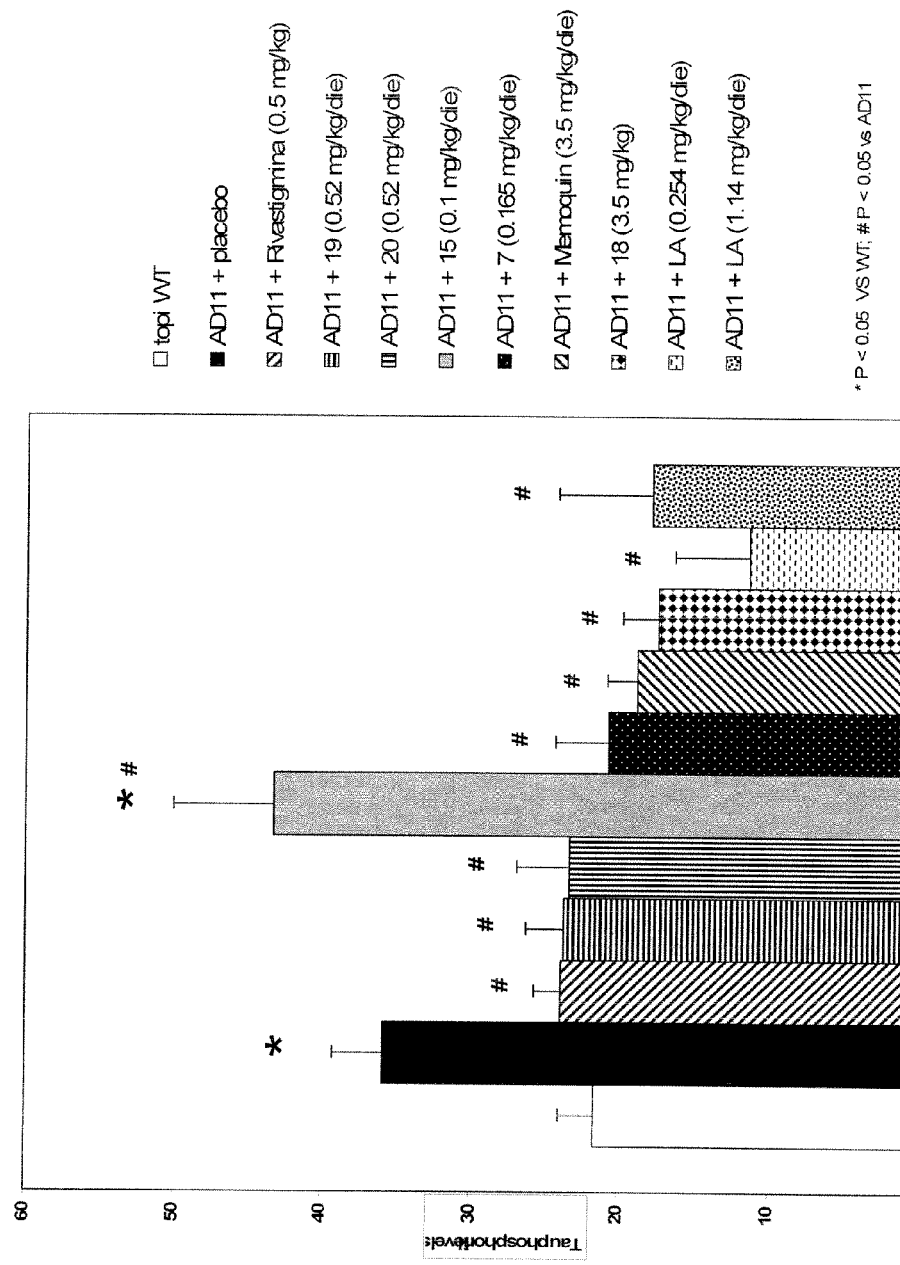
FIG. 4 shows the effects of the compounds on the levels of phosphorylated tau in anti-NGF mice, * and # P<0.05

All the compounds administered recovered the phospho-tau phenotype, with the exception of 15 (FIG. 4).

TABLE 7

| Compound | ChAT | Tau |
|---|---|---|
| 15 | +/− | − |
| 7 | +/− | + |
| Memoquin | +/− | + |
| 18 | + | + |
| Rivastigmine | +/− | + |
| 19 | +/ | + |
| 20 | +/ | + |

TABLE 7-continued

| Compound | ChAT | Tau |
|---|---|---|
| LA | +/ | + |
| LA | +/ | + |

ChAT indicates choline acetyltransferase. WT mice are "wild type" mice.

The invention claimed is:

1. A compound of formula (I):

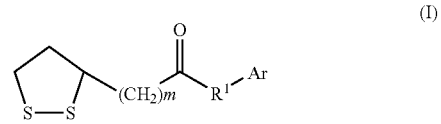

or optically active forms thereof, diastereoisomers thereof, racemic forms thereof, or pharmaceutically acceptable salts thereof, wherein $R^1$ is selected from the group consisting of: $C_2$-$C_9$ alkanediamine, $C_1$-$C_6$ amine and NH; m is an integer greater than zero and lower than eight; $R^1$ comprises a nitrogen linked directly to the carbonyl; Ar is selected from the group consisting of:

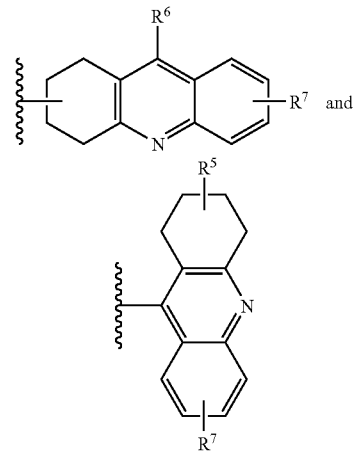

wherein $R^5$ is hydrogen; $R^6$ is selected from the group consisting of: hydrogen and amine; and $R^7$ is selected from the group consisting of: hydrogen C1-C4 alkoxy and halogen.

2. Compound according to claim 1, wherein m is an integer greater than two and lower than five.

3. Compound according to claim 1, wherein m is four.

4. Compound according to claim 1, wherein $R^7$ is selected from the group consisting of: halogen, hydrogen and methoxy; $R^5$ is selected from the group consisting of: hydrogen, amine, nitroalkyl, halogen and hydroxy; $R^1$ is selected from the group consisting of: $C_2$-$C_7$ alkanediamine and $C_1$ amine; and m is greater than zero and lower than five.

5. Compound according to claim 1, wherein Ar has the formula:

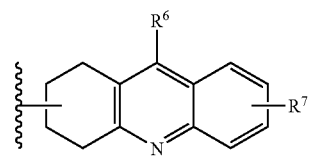

$R^7$ is selected from the group consisting of: hydrogen, $C_1$-$C_4$ alkoxy and halogen; $R^6$ represents an amine; and $R^1$ is selected from the group consisting of: $C_1$ amine and NH.

6. Compound according to claim 5, wherein $R^6$ is selected from the group consisting of: —$NH_2$ and $C_1$-$C_4$ amine.

7. Compound according to claim 5, wherein $R^7$ is a chlorine situated in position 6; $R^6$ represents —$NH_2$; and $R^1$ represents —NH—$CH_2$—, wherein the nitrogen is linked to the carbonylic carbon.

8. Compound according to claim 1, wherein Ar has the formula:

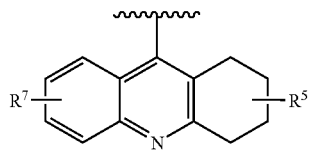

wherein $R^1$ represents a $C_2$-$C_6$ alkanediamine.

9. Compound according to claim 8, wherein $R^1$ represents a $C_3$-$C_4$ alkanediamine.

10. Compound according to claim 8, wherein $R^1$ has the formula —$NR^3$—$R^2$—$NR^4$—, wherein $R^2$ represents a $C_2$-$C_4$ alkyl, and $R^3$ and $R^4$ are selected, each independently of the other, from the group consisting of: hydrogen and methyl.

11. Compound according to claim 10, wherein both $R^3$ and $R^4$ represent hydrogen.

12. Compound according to claim 10, wherein $R^2$ represents —$(CH_2)_3$—.

13. Compound according to claim 8, wherein $R^7$ is selected from the group consisting of: halogen and $C_1$-$C_4$ alkoxy.

14. Compound according to claim 8, wherein $R^7$ represents a halogen.

15. Compound according to claim 8, wherein $R^7$ is situated in position 6.

16. Compound according to claim 8, wherein $R^5$ is selected from the group consisting of: hydrogen, $C_1$-$C_4$ amine, $NH_2$, $C_1$-$C_4$ nitroalkyl, nitro and halogen.

17. Compound according to claim 8, and having the following formula:

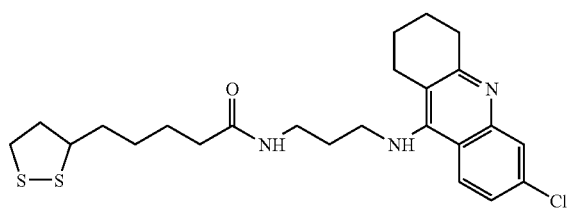

18. Compound according to claim 8, and having the following formula wherein the asymmetric carbon center labeled with R has the (R) configuration

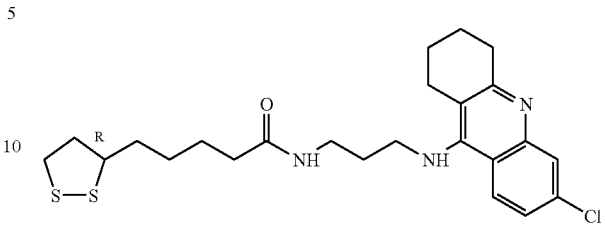

19. A composition comprising a compound of formula (I):

(I)

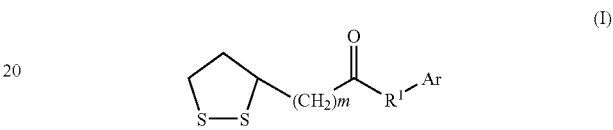

or optically active forms thereof, diastereoisomers thereof, racemic forms thereof, or pharmaceutically acceptable salts thereof, wherein $R^1$ is selected from the group consisting of: $C_2$-$C_9$ alkanediamine, $C_1$-$C_6$ amine and NH; m is an integer greater than zero and lower than eight; $R^1$ comprises a nitrogen linked directly to the carbonyl; Ar is selected from the group consisting of:

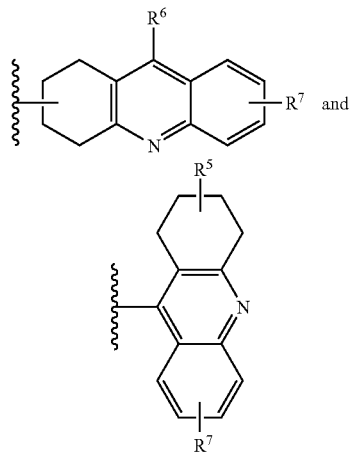

wherein $R^5$ is hydrogen; $R^6$ is selected from the group consisting of: hydrogen and amine; and $R^7$ is selected from the group consisting of: hydrogen C1-C4 alkoxy and halogen; and an excipient and/or a pharmaceutically acceptable diluent.

* * * * *